United States Patent
Palacios et al.

(10) Patent No.: US 6,939,358 B2
(45) Date of Patent: Sep. 6, 2005

(54) APPARATUS AND METHOD FOR APPLYING REINFORCEMENT MATERIAL TO A SURGICAL STAPLER

(75) Inventors: Edward M. Palacios, Flagstaff, AZ (US); Raymond P. Torrez, Flagstaff, AZ (US)

(73) Assignee: Gore Enterprise Holdings, Inc., Newark, DE (US)

( * ) Notice: Subject to any disclaimer, the term of this patent is extended or adjusted under 35 U.S.C. 154(b) by 548 days.

(21) Appl. No.: 10/026,108

(22) Filed: Dec. 20, 2001

(65) Prior Publication Data

US 2003/0120284 A1 Jun. 26, 2003

(51) Int. Cl.⁷ .............................................. A61B 17/08
(52) U.S. Cl. ...................................... 606/151; 606/220
(58) Field of Search ................................ 606/151, 219, 606/220, 75, 213, 215; 206/438–441, 447; 602/54, 58, 59

(56) References Cited

U.S. PATENT DOCUMENTS

| | | | |
|---|---|---|---|
| 4,212,296 A | * | 7/1980 | Schaar .......................... 602/59 |
| 4,394,904 A | * | 7/1983 | Larimore .................... 206/447 |
| 5,088,483 A | * | 2/1992 | Heinecke ...................... 602/52 |
| 5,441,193 A | | 8/1995 | Gravener ..................... 227/176 |
| 5,503,638 A | | 4/1996 | Cooper et al. ................. 623/11 |
| 5,549,628 A | | 8/1996 | Cooper et al. .............. 606/220 |
| 5,575,803 A | | 11/1996 | Cooper et al. .............. 606/151 |
| 5,702,409 A | | 12/1997 | Rayburn et al. ............. 606/151 |
| 5,752,965 A | | 5/1998 | Francis et al. .............. 606/151 |
| 5,810,855 A | | 9/1998 | Rayburn et al. ............. 606/151 |
| 6,071,290 A | | 6/2000 | Compton ..................... 606/151 |

* cited by examiner

*Primary Examiner*—Julian W. Woo
(74) *Attorney, Agent, or Firm*—David J. Johns

(57) ABSTRACT

An apparatus and method used to apply a self-adherent strip of bio-compatible, staple line reinforcement material onto a working surface of a surgical stapler. The apparatus effectively contains and supports reinforcement material during sterilization and shipment. At the point of use, the apparatus provides a simple method for applying the reinforcement material to a variety of staplers. Once the reinforcement material is applied, no excess material remains attached to the stapler thus post-attachment removal of excess material is avoided. The apparatus is simple to manufacture, accommodates a wide variety of reinforcement material shapes and configurations, allows for accurate sizing of the reinforcement material to a variety of stapler jaws, and provides a very low profile package to reduce packaging, shipping, and storage costs.

18 Claims, 25 Drawing Sheets

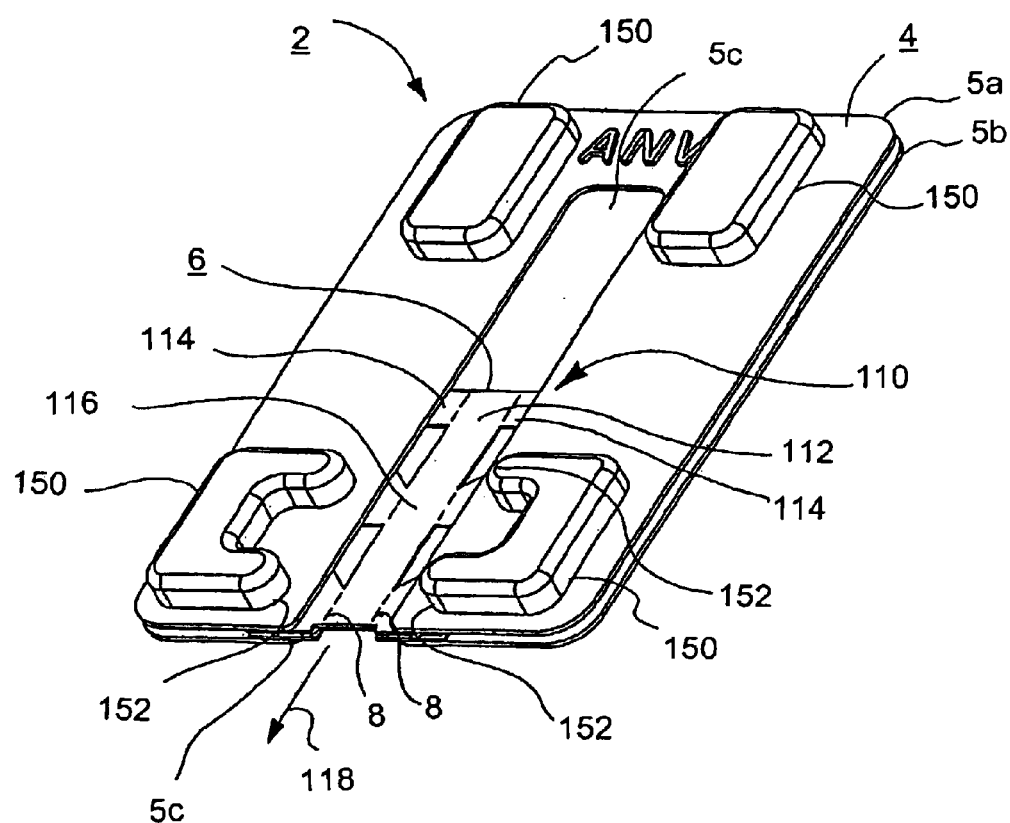

APPARATUS AND METHOD FOR APPLYING REINFORCEMENT MATERIAL TO A SURGICAL STAPLER

FIELD OF THE INVENTION

The present invention relates to surgical staple devices and more specifically to an improved apparatus for applying reinforcing materials to surgical staple devices.

BACKGROUND OF THE INVENTION

One of the more commercially successful innovations in surgical procedures in recent years is the development of surgical stapler devices. These devices are designed to seal or simultaneously cut and seal an extended segment of tissue in a patient, vastly reducing the time and risks of such procedures. Typically, a surgical stapler comprises two stapler arms, one containing two or more lines of multiple staples ("cartridge" or "jaw") and a second containing corresponding means to bend each of the staples into a closed position ("anvil"). For most applications, a surgical blade is included in the device to quickly sever tissue between the lines of staples. Those stapler devices employing a cutting blade are referred to as "anastomotic staplers" and those used without a cutting blade are referred to as "non-anastomotic staplers."

In the operation of a typical anastomotic stapler, the two stapler arms are positioned around tissue to be cut and then locked firmly together. In one motion the surgeon then actuates the stapler device, which simultaneously installs and "sets" two or more lines of staples through the tissue and cuts a line down the middle of the staple lines. In this manner, the physician can quickly cut and seal up to about 8 cm of tissue at a time. This procedure is much faster than using a conventional process of cutting with scissors or a scalpel and then laboriously sealing the incision with sutures. As a result, patient care is dramatically improved by minimizing bleed time from the surgical site and significantly increasing the speed with which an operation can be completed.

For most procedures, the use of bare staples, with the staples in direct contact with the patient's tissue, is generally acceptable. The integrity of the tissue itself will normally serve to prevent the staples from tearing out of the tissue and compromising the seam before healing has occurred. However, in certain circumstances the tissue that is being sealed is too fragile to securely hold the staples in place. In these instances, the tissue will tend to rip at or near the staple lines, slowing healing and possibly leading to serious complications.

One area where fragile tissue is of particular concern is the use of stapler devices in lung tissue, and especially lung tissue that is affected by emphysema or similar condition. Diseased lung tissue is very fragile and, in extreme cases, will easily tear through unprotected staple lines. With the growing use of surgical staplers in operations on diseased lung tissues such as bullectomies and volume reduction procedures, it has become increasingly important to develop some reliable means to protect fragile tissue from tissue tears due to surgical staples or surgical stapling procedures.

A surgical stapler reinforcement material is disclosed in U.S. Pat. No. 5,441,193 to Gravner. A resilient strip of material is pre-attached to a stapler jaw and/or anvil. The surgical staples are fired and set through the tissue and resilient material which strengthens and reinforces the staples. The resilient material can be pre-attached to the stapler by the use of adhesives or by mechanical means such as grooves, slots or projections. Once the staples are fired, the reinforcement material is released from the stapler jaw and/or anvil. Since the reinforcement material of Gravner is pre-attached to the stapler, it is only suited for those staplers specifically designed to receive the configuration of Gravner. Due to the integral nature of the stapler and the reinforcement material, no carrier facilitating the loading of the reinforcement material onto the stapler is required.

In U.S. Pat. Nos. 5,503,638, 5,575,803 and 5,549,628 to Cooper et al., an alternate configuration of a staple reinforcement material is disclosed. In these patents, a disposable sleeve is attached to the reinforcement material. The sleeve is formed into a three-sided "U" shape, which is sized to slip-fit over a stapler jaw or anvil. The fourth side of the sleeve is comprised of the reinforcement material which contacts the active surface of stapler jaw or anvil. The reinforcement material is releasibly attached to the disposable sleeve, for example by a suture. After the staples are fired, the reinforcement material is released from the disposable sleeve by unthreading the suture. The disposable sleeve must then be removed and discarded. Such a reinforcement material is more suited for open surgical procedures. In laparoscopic procedures, the sleeve surrounding the stapler jaw and anvil can interfere with the trocar. This requires the use of oversized trocars and removal of the suture attachment through the trocar. The disposable sleeve must also be captured and withdrawn through the trocar.

Staple line reinforcement devices are commercially available from W. L. Gore & Associates, Inc., Flagstaff, Ariz., under the trademark SEAMGUARD®. Such staple line reinforcement devices are described in U.S. Pat. Nos. 5,702,409 and 5,810,855 to Rayburn et al. These devices comprise a material formed into a sleeve, which is sized to slip-fit over a stapler jaw or anvil. The sleeve incorporates tear lines or other means to allow easy separation of the disposable portions of the device, from the portions secured by the fired staples. Retrieval means, such as a suture, capture and allow retrieval of the disposable portions of the device. In laparoscopic procedures, there are concerns similar to those discussed in Cooper.

An alternate staple line reinforcement device is commercially available from Bio-Vascular, Inc., Saint Paul, Minn. under the trademark PERI-STRIPSDRY™. U.S. Pat. No. 5,752,965 to Francis et al. describes such a reinforcement device and a carrier used to present and load the device onto a stapler. This reinforcement material, comprising dried and treated bovine pericardium, is in the form of a strip sized to cover the desired part of the stapler. One or two of these pericardial strips are releasibly attached to the carrier. Just prior to use, an adhesive gel is applied to the pericardial strips. The gel softens the strips and acts as an adhesive to allow temporary attachment to the stapler. The stapler is then self-aligned to the carrier, the jaws are closed upon the pericardial strips, and the gel adheres the strips to the stapler jaws. Unlike the slip-fit tubes of other reinforcement devices, the pericardial strips do not surround the stapler jaws. In order to provide for application of the strips, the Francis et al. patent teaches use of an apparatus having multiple deep guide channels to self-direct the surgical fastener into contact with the reinforcement material, and integral pressure equalization means in the form of resilient foam or similar material attached to the receiving area of the applicator card to aid in establishing a uniform adherence of the reinforcement strips to the surgical fastener.

There are a number of serious deficiencies with the Francis et al. apparatus. First, the use of bovine pericardium material is undesirable since this material requires preparation prior to use and must be kept moist to prevent embrittling and cracking when the staples are fired. Thus staples must be fired soon after mounting of the reinforcement material, limiting the ability to prepare multiple staplers with reinforcement devices prior to use. The implantation of bovine material also raises concerns associated with bovine maladies that can be transmitted to humans, such as Creutzfelt-Jakob Disease (CJD) or Bovine Spongiform Encephalopathy (BSE). Second, the carrier apparatus of Francis et al. may function adequately well for its intended purpose, but it is believed to be overly bulky in design due to the requirement for deep perpendicularly mounted guide channels. Additionally, the apparatus of Francis et al. does not optimize material adherence to the surgical stapler. For instance, the method of attachment of the reinforcement material to the stapler arms is difficult to engineer among a variety of staple arm designs—thus requiring use of an integral layer of resilient foam to attempt to compensate for inaccurate sizing. Not only does the pressure equalizing foam provide less than optimal adherence, but due to the fact that Francis et al. teach that the foam is removed along with the reinforcement material upon application, additional steps are required for the surgical staff to remove and discard the foam prior to the insertion of the stapler into the patient.

An improved staple line reinforcement device would have desirable features that allow lower profile insertion and would not require the removal of excess reinforcement material following deployment. In addition, it would be desirable to provide a reinforcement material that provides effective and simple "one-step" attachment to a stapler with minimal pre- and post-attachment requirements.

SUMMARY OF THE INVENTION

The present invention is an apparatus and method used to apply a self-adherent strip of bio-compatible, staple line reinforcement material onto a working surface of a surgical stapler. The apparatus effectively contains and supports the self-adherent, reinforcement material during sterilization and shipment. At the point of use, the apparatus provides a simple method for applying the self-adherent reinforcement material to a variety of staplers. Once the reinforcement material is applied, no excess material remains; thus post-attachment removal of excess material is avoided. The apparatus is simple to manufacture, accommodates a wide variety of reinforcement material shapes and configurations, and allows for accurate sizing of the reinforcement material to a variety of stapler jaws.

The preferred apparatus of the present invention comprises a package for applying surgical staple reinforcement material to arms of a surgical stapler comprising: an application card including a landing; a staple reinforcement material having a first portion adapted to be attached to the arms of the surgical stapler, a second portion adapted to be attached to the application card, and tear lines separating the first portion and the second portion. Adhesive is provided (such as by providing a tacky material pre-applied to the reinforcement material, or as a separate material applied at the time of use), to attach the first portion of staple reinforcement material to the stapler arms. The second portion of the staple reinforcement material is attached to application card so as to position the first portion over the landing for alignment with the stapler arms for application. The tear lines on the staple reinforcement material serve to allow the first portion of staple reinforcement material to be separated laterally from the landing once the adhesive attaches the staple reinforcement material to the arms of the surgical stapler.

It has been demonstrated that the process of lateral separation of the reinforcement material from the application card, causing a shearing of the material across the landing under pressure, provides a secure and uniform application of the material to a variety of shapes and sizes of the stapler arms.

These and other benefits of the present invention will be appreciated from review of the following description.

BRIEF DESCRIPTION OF THE DRAWINGS

The operation of the present invention should become apparent from the following description when considered in conjunction with the accompanying drawings, in which:

FIG. 14 is a three-quarter side isometric view of the apparatus of the present invention according to Example 2, comprising an application card and a strip of staple line reinforcement material having a first removable portion and a second retained portion;

DETAILED DESCRIPTION OF DRAWINGS

The apparatus of the present invention is used to package and facilitate loading of a self-adherent staple line reinforcement material onto a stapler. The apparatus has a generally planar form with a multi-layered structure which "sandwiches" and contains one or more strips of reinforcement material. To attach the reinforcement material to a stapler, open stapler arms are positioned over the exposed reinforcement material, the stapler arms are closed to compress upon the reinforcement material, and the closed arms are then pulled laterally away from the application card. This process of lateral separation, applying pressure while the reinforcement material is sheared across the landing in a lateral movement, has proven to be highly effective at creating a secure and uniform attachment of the reinforcement material to the stapler arms. Thus, in one step the reinforcement material can be properly adhered to the stapler arms. The remaining, single piece application card is then discarded.

Figure 1A:
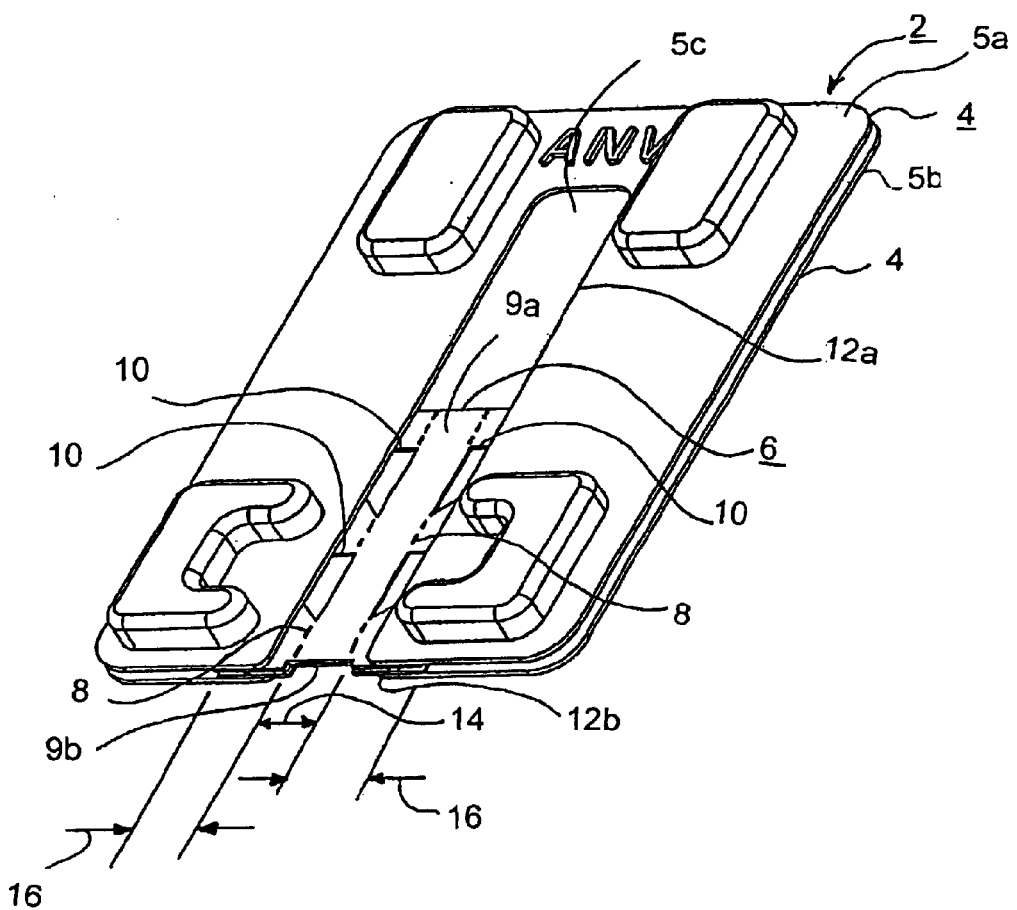
FIGS. 1A and 1B are three-quarter side isometric views of two embodiments of the apparatus of the present invention, comprising an application card and a strip of staple line reinforcement material.
Figure 1B:
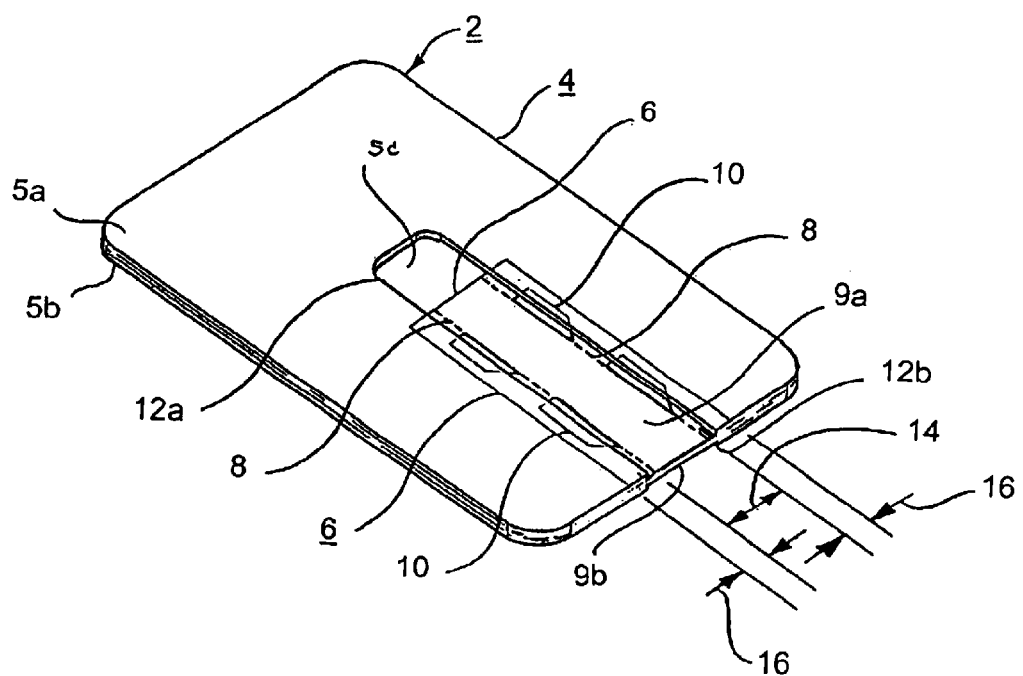

FIGS. 1A and 1B are isometric views of the apparatus 2 of the present invention. Shown are an application card 4 having a first portion 5a, a second portion 5b and a support layer 5c sandwiched between the first and second portions; reinforcement material 6, having formed therein tear lines 8, and tear reliefs 10; a first aperture 12a; and a second aperture 12b. The reinforcement material 6 comprises two general portions. The application card holds and retains the portion or portions of reinforcement material outside of the tear lines 8. The widths of these outside portions are depicted by dimension 16. The other portion comprises the operative portions 9a and 9b of reinforcement material that is actually applied to the stapler arms. The operative portions have a width 14 sized to match the width of a specific stapler.

To load the reinforcement material onto a stapler, the open stapler arms are positioned within the apertures 12a and 12b over the operative portions 9a and 9b of the reinforcement material. The arms are then closed and squeezed onto the operative portions 9a and 9b. The operative portions are then separated along the tear lines 8 and along the tear reliefs 10 when the closed stapler is withdrawn laterally from the application card 4.

Staple line reinforcement strips suitable for use with the present invention can be fabricated from any material having acceptable bio-compatibility and mechanical properties. A preferred base material is expanded polytetrafluoroethylene ("ePTFE") such as that disclosed in U.S. Pat. No. 5,810,855 to Rayburn et al. A layer of tacky, adhesive material can be added to the base material to form a composite staple line reinforcement material. This composite material therefore has an adhesive surface which provides a releasable attachment to a stapler jaw or anvil and an opposing low friction surface. The low friction surface allows the reinforcement material to slide relative to the support layer of the application card while being pulled laterally when attached to the closed stapler jaws. The adhesive may comprise any bio-compatible, sterilization-compatible, tacky substance, whether inorganic, organic, natural or synthetic, that is capable of bonding to other substances by surface attachment, including rubbers, silicones, polyurethanes, or fluoropolymers. The adhesive can be pre-applied to the reinforcement material or applied at the point of use. For certain adhesives, it may be desirable to cover the pre-applied adhesive with release paper or similar material to protect the adhesive layer during shipping and handling. The release paper can then be removed prior to use.

Figure 2:
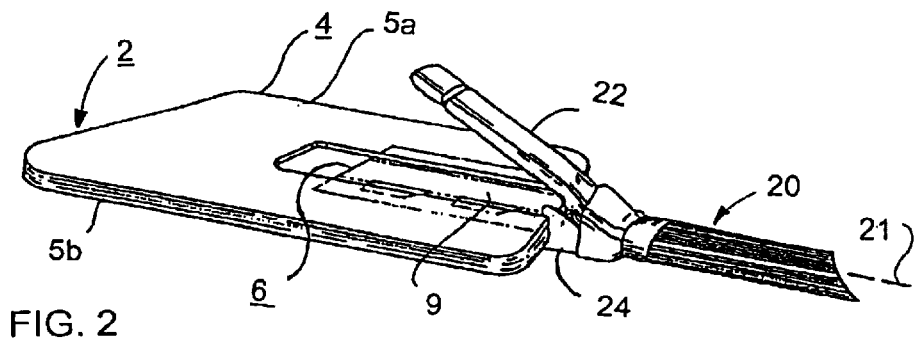
FIGS. 2 through 5 are three-quarter perspective views showing the sequence of loading a self-adhering reinforcement material from an application card of the present invention onto the jaws of a surgical stapler.
Figure 3:
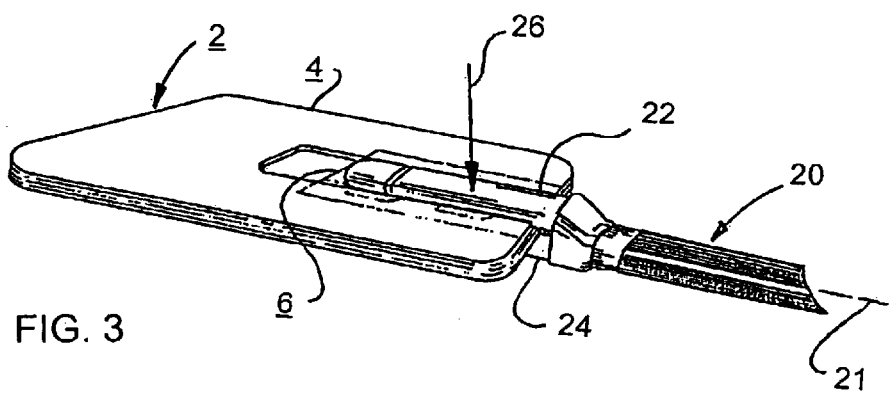
Figure 4:
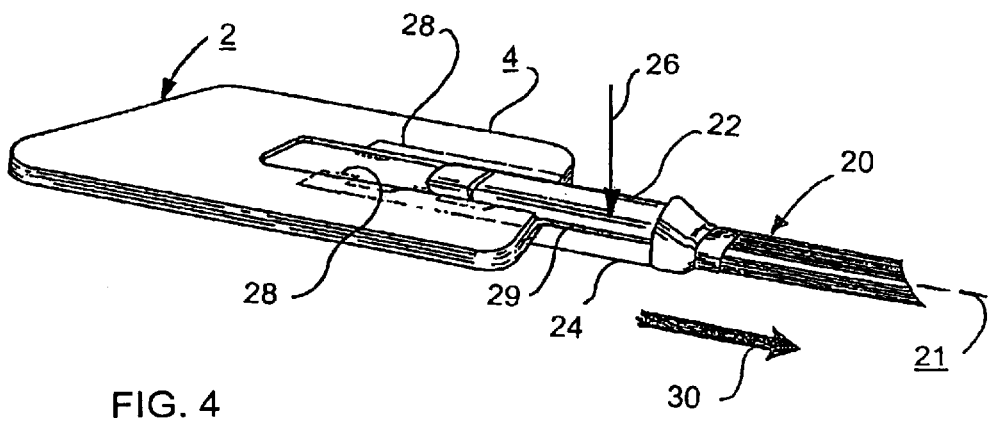

The sequence and apparatus of the present invention used to attach reinforcement material to a stapler is depicted in FIGS. 2 through 5. Shown in FIG. 2 is an apparatus 2 of the present invention, application card 4, reinforcement material 6, a stapler assembly 20, having an anvil portion 22, a cartridge or "jaw" portion 24 and a longitudinal axis 21. Together the anvil portion 22 and the cartridge portion 24 comprise the arms of the stapler 20. The open anvil and jaw of the stapler are positioned over the operative portion 9 of the reinforcement material 6. As shown in FIG. 3 the stapler anvil and jaw are then closed, which applies a compressive force 26 onto the self-adherent reinforcement material 6. While maintaining the compressive force 26, the stapler assembly 20 with closed jaws is laterally pulled away from the application card 4 in the direction 30, as shown in FIG. 4. Additional compressive force may be applied by manually holding the arms against the card during separation.

The "lateral" direction comprises any relative sideways motion that pulls the reinforcement material essentially parallel to the longitudinal axis 21 of the stapler arms. The "lateral" direction can be a pulling motion, as shown, or a "pushing" motion applied in the opposite direction towards the application card. As the stapler assembly 20 is moved in the lateral direction 30, the captured portion of the reinforcement material 29 is firmly compressed against the stapler surfaces and simultaneously separated from the retained portions 28.

Figure 5:
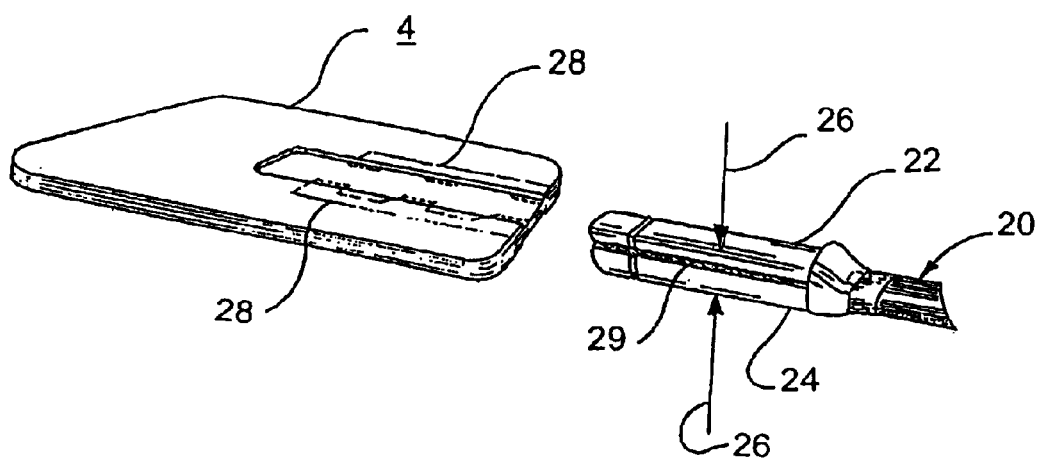

As shown in FIG. 5, the stapler assembly 20 has been completely withdrawn from the application card 4. The self-adherent reinforcement material 29 is captured between the anvil 22 and the cartridge 24. The single-piece application card 4 is discarded and the stapler assembly is then ready for use, such as through insertion into a laproscopic or thoracoscopic trocar.

The procedure depicted in FIGS. 2 through 5 can be used to load one or more strips of self-adherent reinforcement material onto a stapler assembly. The magnitude of the compressive force 26 is dictated by the specific stapler design and in some cases by the amount of squeezing force applied to the stapler handle. Various staplers employ different amounts of mechanical advantage between the gripping handles and the staple jaws. As has been noted, additional compressive force can be provided, such as through manual or clamp pressure applied directly to the stapler arms.

Figure 6:
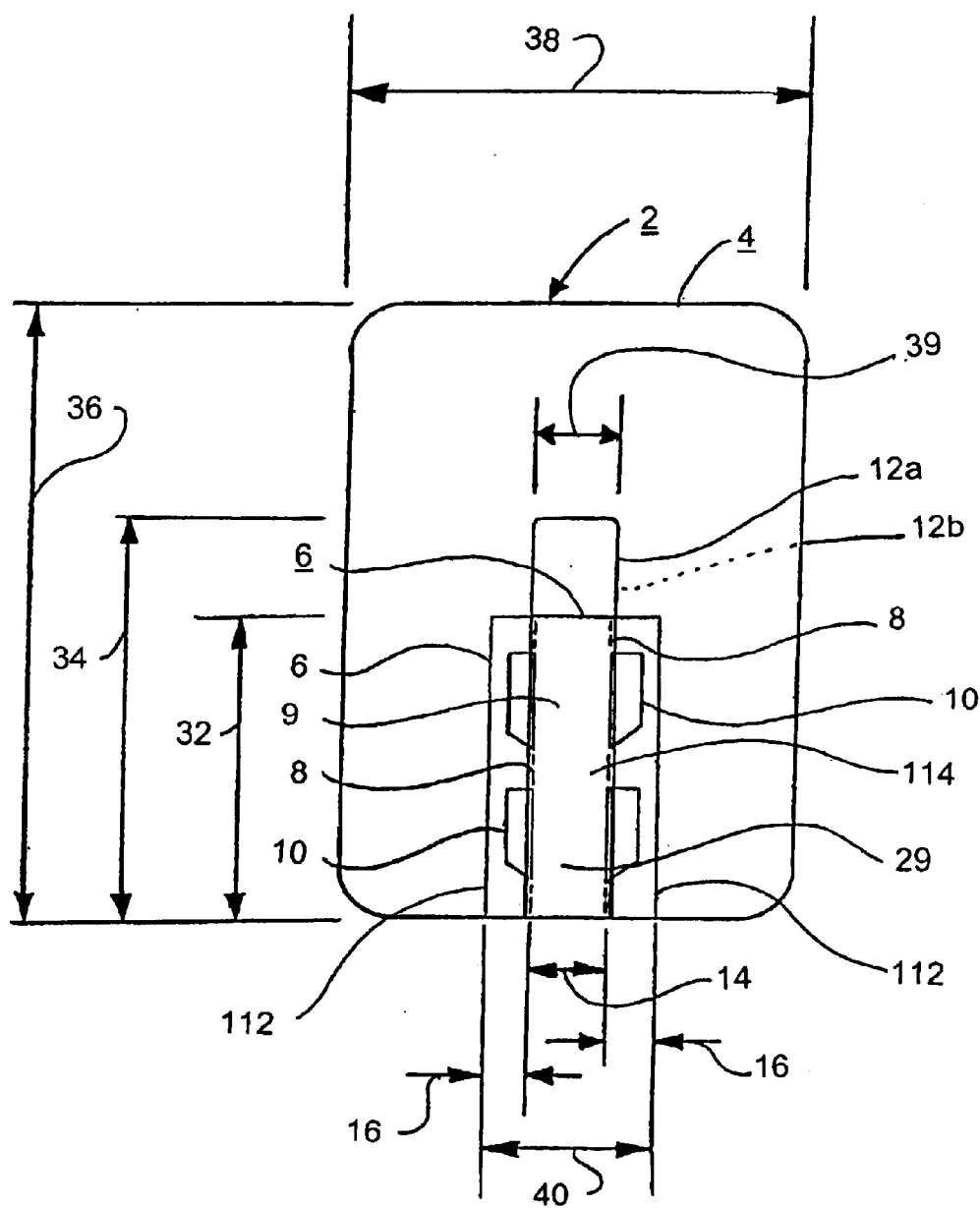
FIG. 6 is a top plan view of the apparatus of the present invention, having an overall length, width, an aperture having a length and width.

FIG. 6 is a top view of a preferred embodiment of the apparatus 2 of the present invention. Shown is an application card 4, reinforcement material 6, tear lines 8, tear reliefs 10, and a first aperture 12a and second aperture 12b. The widths of the retained portions of the reinforcement material are depicted as dimension 16, the overall width of the reinforcement material is depicted as dimension 40, and the width of the operative portion 9 of the reinforcement material is depicted as dimension 14. The widths 16 of the retained portions are selected to provide adequate attachment to the card 4 during sterilization, shipment, and during separation and removal of the operative portion 29.

Methods of attaching the reinforcement material to the card include, but are not limited to, adhesive bonding, frictional interference, ultrasonic or thermal welding or mechanical attachment with holes, cut-outs or other features incorporated into the reinforcement material and/or card. The preferred attachment method is using frictional interference as shown and described herein.

Typical widths 14 of the removable portion of the reinforcement material relate to a specific stapler or group of similarly dimensioned staplers. The width 14 is typically the width of the particular stapler, minus approximately 0.5 mm or less, depending upon the specific stapler design. Some commercially available staplers have different widths of anvils and cartridges which optimally may employ two different widths of reinforcement materials. The overall width 40 of the reinforcement material is the accumulation of dimensions 14 and 16. The length 32 of the reinforcement material is again dependent on the specific stapler selected. Typical length 32 approximates the length of a specific stapler jaw, minus some clearance, for example, of about 1 to 10 mm.

A single package of the present invention can be dimensioned to adapt to a specific stapler or to a family of similarly dimensioned staplers. Dimensions of the removable portion can be altered to adapt to a specific stapler and be retained with a commonly dimensioned card. Thus a single card can be dimensioned for use on a variety of staplers, each requiring differently dimensioned reinforcement materials.

The length 34 of the apertures 12a and 12b are typically the length 32 plus about 10 mm or more. The length 34 of the apertures can range from about 25 mm to about 130 mm. For example, the length 34 can be about: 25 mm, 30 mm, 35 mm, 40 mm, 45 mm, 50 mm, 55 mm, 60 mm, 65 mm, 70 mm, 75 mm, 80 mm, 85 mm, 90 mm, 95 mm, 100 mm, 105 mm, 110 mm, 115 mm, 120 mm, 125 mm, or 130 mm. Preferably the length 34 of the apertures can range from about 50 to about 100 mm. For example, the length 34 can be about: 50 mm, 55 mm, 60 mm, 65 mm, 70 mm, 75 mm, 80 mm, 85 mm, 90 mm, 95 mm, or 100 mm. Most preferably, the length 34 can be about 85 to 95 mm.

The width 39 of the apertures 12a and 12b is primarily dictated by the width 14 of the removable portion of the reinforcement material. A typical width 39 of the apertures is the width 14 plus about 4 mm. About 0.1 to 10 mm can be added to the width 14 to produce a suitable aperture width. The width 39 of the apertures 12a and 12b can range from about 5 mm to about 30 mm. For example, width 39 of the apertures can be about: 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, or 30 mm. Preferably the width 39 of the apertures can range from about 10 mm to about 20 mm. Most preferably, a width 39 can be about 14 mm to 116 mm.

A typical card length 36 can range from about: 50 mm to about 200 mm. For example, card length 36 can be about: 50 mm, 55 mm, 60 mm, 65 mm, 70 mm, 75 mm, 80 mm, 85 mm, 90 mm, 95 mm, 100 mm, 105 mm, 110 mm, 115 mm, 120 mm, 125 mm, 130 mm, 135 mm 140 mm, 145 mm, 150 mm, 155 mm, 160 mm, 165 mm, 170 mm, 175 mm, 180 mm, 185 mm, 190 mm, 195 mm, 200 mm, or 205 mm. Preferably, the card length 36 can range from about 75 mm to 130 mm. Most preferably, a card length 36 can be about 100 mm to 106 mm.

A typical card width 38 can range from about 25 mm to about 150 mm. For example, card width 38 can be about: 25 mm, 30 mm, 35 mm, 40 mm, 45 mm, 50 mm, 55 mm, 60 mm, 65 mm, 70 mm, 75 mm, 80 mm, 85 mm, 90 mm, 95 mm, 100 mm, 105 mm, 110 mm, 115 mm, 120 mm, 125 mm, 130 mm, 135 mm 140 mm, 145 mm, or 150 mm. Preferably, card width 38 can range from about 50 mm to about 100 mm. Most preferably, a card width 38 can be about 69 mm to 73 mm.

Example dimensions relating to a reinforcement material, tailored to adapt to a Model ETS 45 stapler, available from Ethicon, Somerville, N.J., are depicted in FIG. 6. The reinforcement material shown in FIG. 6 can be specifically dimensioned to adapt to the stapler anvil or dimensioned to adapt to the stapler cartridge. Both configurations of reinforcement materials can be presented in a single package of the present invention. As shown in FIG. 6, an overall length 32 of the reinforcement material, adapted for the anvil portion, can range from about 5 mm to about 120 mm. For example reinforcement material length 32 can be about: 5 mm, 10 mm, 15 mm, 20 mm, 25 mm, 30 mm, 35 mm, 40 mm, 45 mm, 50 mm, 55 mm, 60 mm, 65 mm, 70 mm, 75 mm, 80 mm, 85 mm, 90 mm, 95 mm, 100 mm, 105 mm, 110 mm 115 mm, or 120 mm. Preferably reinforcement material length 32 can be about: 20 mm, 25 mm, 30 mm, 35 mm, 40 mm, 45 mm, 50 mm, 55 mm, 60 mm, 65 mm, or 70 mm. Most preferably, reinforcement material length 32 can be about 42 mm to 46 mm.

The overall width 40 of the reinforcement material adapted for the anvil portion can range from about 10 mm to 50 mm. For example reinforcement material width 40 can be about: 10 mm, 20 mm, 25 mm, 35 mm, 40 mm or 50 mm. Most preferably, reinforcement material width 40 can be about 29 mm to 32 mm.

The width 14 of the removable portion 112 of the reinforcement material adapted for the anvil portion can range from about 2 mm to about 20 mm. For example the width 14 of the removable portion 112 of the reinforcement material can be about: 2 mm, 4 mm, 6 mm, 8 mm, 10 mm, 12 mm, 14 mm, 16 mm, 18 mm, or 20 mm. Preferably the width 14 of the removable portion 112 of the reinforcement material can be about 5 mm to 15 mm. Most preferably, the width 14, of the removable portion 112, of the reinforcement material can be about 9.5 mm to 12 mm.

The width 16 of the retained portion 114 of the reinforcement material adapted for the anvil portion can range from about 2 mm to about 20 mm. For example, the width 16 of the retained portion 114 of the reinforcement material can be about: 2 mm, 4 mm, 6 mm, 8 mm, 10 mm, 12 mm, 14 mm, 16 mm, 18 mm, or 20 mm. Preferably the width 16 of the retained portion 114 of the reinforcement material can be about 5 mm to about 15 mm. Most preferably, the width 16 of the retained portion 114 of the reinforcement material can be about 9 mm to 11 mm.

As further shown in FIG. 6, an overall length 32 of the reinforcement material, adapted for the cartridge portion of a Model ETS 45 stapler, available from Ethicon, Somerville, N.J., can range from about 5 mm to 120 mm. For example, reinforcement material length 32 can be about: 5 mm, 10 mm, 15 mm, 20 mm, 25 mm, 30 mm, 35 mm, 40 mm, 45 mm, 50 mm, 55 mm, 60 mm, 65 mm, 70 mm, 75 mm, 80 mm, 85 mm, 90 mm, 95 mm, 100 mm, 105 mm, 110 mm, 115 mm, or 120 mm. Preferably reinforcement material length 32 can be about 20 mm to 70 mm. Most preferably, reinforcement material length 32 can be about 50 mm to 55 mm.

The overall width 40 of the reinforcement material adapted for the cartridge portion can range from about 10 mm to 50 mm. For example reinforcement material width 40 can be about: 10 mm, 15 mm, 20 mm, 25 mm, 30 mm, 35 mm, 40 mm, 45 mm, or 50 mm. Preferably reinforcement material width 40 can be about 15 mm to 45 mm. Most preferably, reinforcement material width 40 can be about 29 mm to 32 mm.

The width 14 of the removable portion 112 of the reinforcement material adapted for the cartridge portion can range from about 2 mm to about 20 mm. For example the width 14 of the removable portion 112 of the reinforcement material can be about: 2 mm, 4 mm, 6 mm, 8 mm, 10 mm, 12 mm, 14 mm, 16 mm, 18 mm, or 20 mm. Preferably the width 14 of the removable portion 112 of the reinforcement material can be about 5 mm to 15 mm. Most preferably, the width 14 of the removable portion 112 of the reinforcement material can be about 8.5 mm to 10.5 mm.

The width 16 of the retained portion 114 of the reinforcement material adapted for the cartridge portion can range from about 2 mm to about 20 mm. For example the width 16 of the retained portion 114 of the reinforcement material can be about: 2 mm, 4 mm, 5 mm, 8 mm, 10 mm, 12 mm, 14 mm, 16 mm, 18 mm, or 20 mm. Preferably the width 16 of the retained portion 114 of the reinforcement material can be about 5 mm to 15 mm. Most preferably, the width 16 of the retained portion 114 of the reinforcement material can be about 9.5 mm to 11.5 mm.

One of the distinct advantages of the package of the present invention is that the sizes of the card itself are not critical to the proper operation of the package. Unlike the use of material specific guide channels described in U.S. Pat. No. 5,752,964 to Francis et al., a single card of the present invention can be used for a wide variety of reinforcement material lengths, widths, and thicknesses.

Figure 7A:
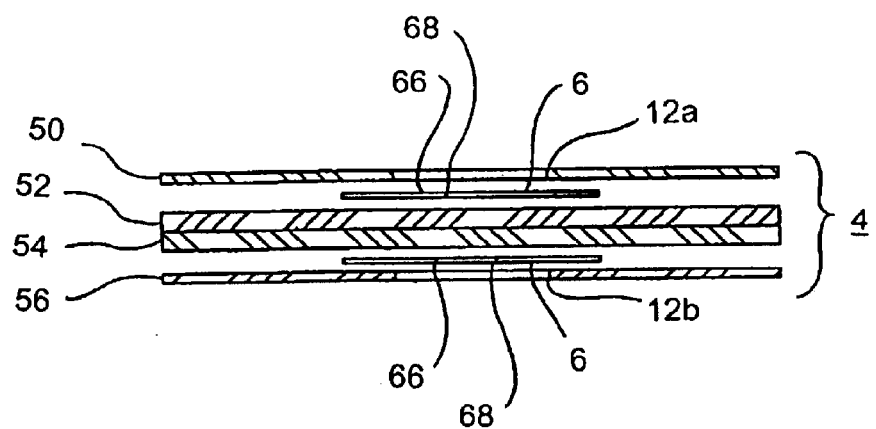
FIGS. 7A and 7D are front edge views showing the multi-layered construction of the application card of the present invention.
Figure 7D:
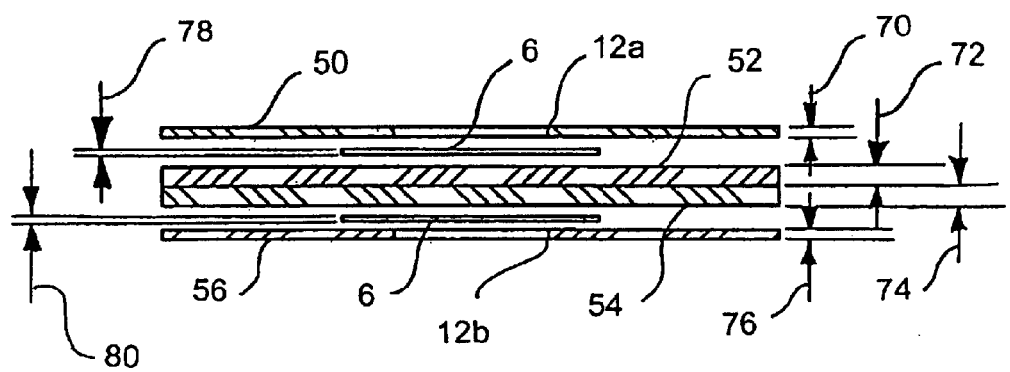

FIGS. 7A and 7D are front edge views of the apparatus shown in FIG. 6. Shown in FIG. 7A is a multi-layer construction of an application card 4, having first outer layer 50, a first support layer 52, a second support layer 54, a second outer layer 56, a first layer aperture 12a, and a second aperture 12b. A strip of self-adherent reinforcement material 6 is sandwiched and constrained between the first outer layer 50 and the first support layer 52. The reinforcement material 6 has a self-adhering surface 66 and an opposing low friction surface 68. The self-adhering surface 66 is oriented to face toward the top layer 50. The reinforcement material 6 is exposed through the first layer aperture 12a. A second strip of self-adhering reinforcement material can be similarly sandwiched and constrained between the second outer layer 56 and the second support layer 54. This second strip of reinforcement material is oriented with a self-adhering surface 66 facing the second outer layer 56 and a low-friction surface 68 facing the second support layer 54. A second aperture 12b exposes the constrained strip of reinforcement material.

The combination of a support layer and an aperture, which exposes a surface of a reinforcement material, forms a landing. Thus, in this embodiment the "landing" comprises a first layer having an aperture, which exposes a first surface of reinforcement material, combined with a support layer in contact with an opposing surface of the reinforcement material. For example in FIG. 7A, a landing comprises the first layer 50 having an aperture 12a, which exposes a first surface 66 of a reinforcement material 6, combined with a support layer 52 in contact with an opposing surface 68 of the reinforcement material. A second "landing" is formed by the combination of the second layer 56, aperture 12b, first surface 66 and opposing surface 68 of the reinforcement material 6 and the support layer 54. The reinforcement material can be attached to the first layer, to the support layer, or to both layers.

Figure 7B:
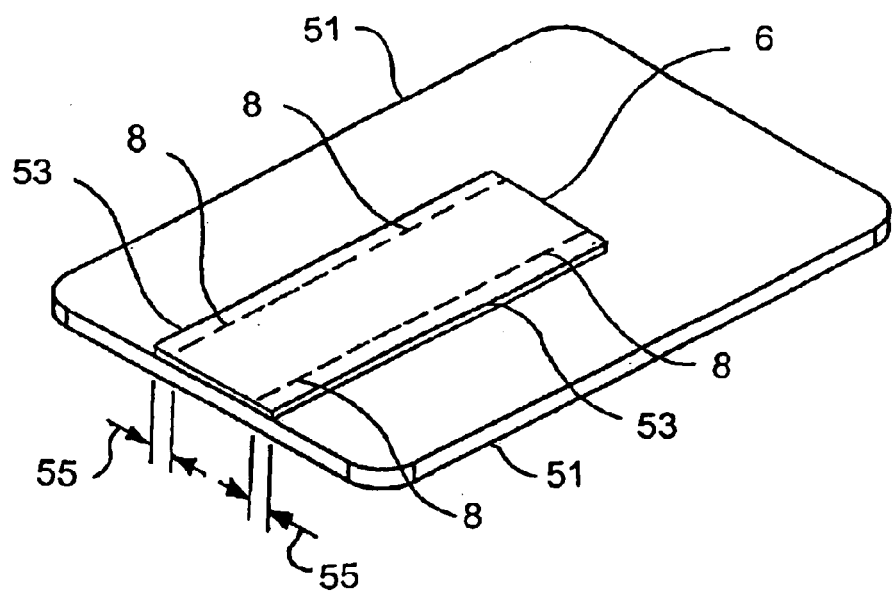
FIGS. 7B and 7C are three-quarter side isometric views of support layers with attached reinforcement materials, defining an alternate configurations of a landing.
Figure 7C:
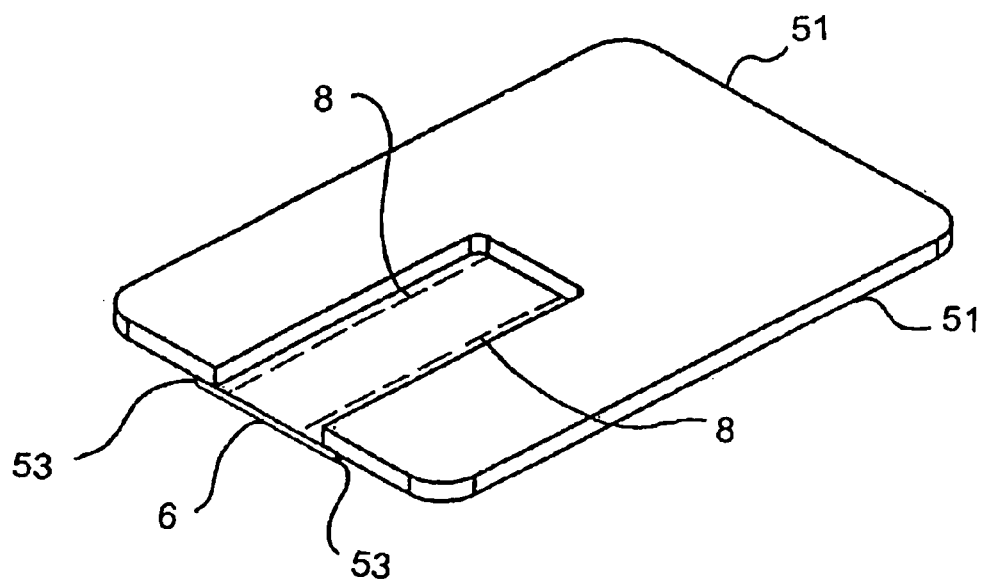

It should be appreciated that the effective "landing" for the present invention may comprise any of a variety of constructions whereby the reinforcement material is held next to a surface against which stapler arms can compress for attachment. For example, an alternate configuration of a "landing" is depicted in FIG. 7B. Shown are a support layer 51, reinforcement material 6, tear lines 8, and attachment areas shown as edges 53 and attachment widths 55. In this configuration, the reinforcement material 6 is attached to the support layer 51 along the edge 53, and along the width 55. The first layer with an aperture is therefore eliminated. In this configuration a landing is defined as reinforcement material with tear lines, partially attached to a support layer. Shown in FIG. 7C is an alternate configuration of a support layer 51 a reinforcement material 6, tear lines 8, and attachment areas shown as edges 53. In this configuration, the reinforcement material 6 is attached to the support layer 51 along the edge 53.

The layers 50, 52, 54 and 56 (FIGS. 7A and D) of the application card 4 can be fabricated from any non-toxic material having sufficient strength and the ability to withstand steam, ETO, or other desired sterilization techniques. Such materials include, but are not limited to, polyethylene and polycarbonates, such as Makrofol R PCEE-112-8905, or GE Lexan R 8040. It is believed desirable that the support layer comprise a fairly hard material, e.g., one having a Shore D durometer of about 40 or more.

The layers 50, 52, 54 and 56 of the application card 4 and the disposable portions of the reinforcement material can be laminated and affixed to each other after the reinforcement material is properly positioned within the apertures 12a and 12b. Heat staking, press-fit tabs, ultrasonic welding, adhesives or other methods can be used to affix the multiple layers together. The support layers 52 and 54 can be combined into a single layer. The thickness of this single or combined layers 52 and 54 can be tailored to accommodate various gaps between the jaws and anvils of different stapler designs. The apertures 12a and 12b can have different profiles and shapes. For example, the first aperture 12a can be wider and/or longer than the second aperture 12b to accommodate a specific stapler design. The apertures also can be offset relative to each other. For example, referring to FIG. 6, the first aperture 12a can be offset to one side of the second aperture 12b to accommodate a specific stapler design. The application card can also be configured to present a multitude of reinforcement strips or be configured to present reinforcement strips having different properties. For example, a first strip can comprise a material that is different from the second strip material. Alternately, two strips of reinforcement materials can have a different thickness, width, and/or shape.

A thickness of each of the multiple layers of the card 4 is shown in FIG. 7D. The thickness 70, 72, 74 and 76 of the individual layers can range from about 0.1 mm to about 3.0 mm. For example, thickness 70, 72, 74, 76, can be about: 0.1 mm, 0.5 mm, 1.0 mm, 1.5 mm, 2.0 mm, 2.5 mm, 3.0 mm, or 3.5 mm. Preferably, thickness 70, 72, 74 and 76 of the individual layers can range from about 0.5 mm to about 1.5 mm. Most preferably, a thickness 70, 72, 74 and 76 of the individual layers can be about 0.7 mm to 0.8 mm.

A typical thickness 78 and 80 of a reinforcement material 6 can range from about 0.1 mm to about 1 mm or more, depending upon specific stapler configurations and reinforcement materials. For example, thickness 78 and 80 of a reinforcement material 6 can be about: 0.1 mm, 0.2 mm, 0.3 mm, 0.4 mm, 0.5 mm, 0.6 mm, 0.7 mm, 0.8 mm, 0.9 mm, or 1 mm. Preferably, thickness 78 and 80 of a reinforcement material 6 can be about 0.25 mm to 0.75 mm. Most preferably, thickness 78 and 80 of a reinforcement material 6 can be about 0.35 mm to 0.5 mm.

A self-adhering adhesive layer can be laminated onto the reinforcement material to allow attachment of the reinforcement material to the package of the present invention and to a stapler arm. An example of a material for such an adhesive layer is MED 6340, medical grade, two-part silicone available from NuSil, Carpinteria, Calif. The two-part silicone is mixed and blended according to the manufacturer's instructions, and applied by brush, pouring, or spreading onto a layer of reinforcement material. The silicone is then cured, for example heated in an oven set at 150° C. for about 2 hours. The resultant cured silicone has tacky, soft and compliant properties suitable for a self-adhering layer.

A typical thickness of a self-adhering layer can range from about 0.01 mm to about 1 mm or more. For example, a thickness of a self-adhering layer can be about: 0.05 mm, 0.1 mm, 0.15 mm, 0.2 mm, 0.25 mm, 0.3 mm, 0.35 mm, 0.4 mm, 0.45 mm, 0.5 mm, 0.55 mm, 0.6 mm, 0.65 mm, 0.7 mm, 0.75 mm, 0.8 mm, 0.85 mm, 0.9 mm, 0.95 mm, or 1 mm. Preferably, a thickness of a self-adhering layer can be about 0.05 mm to 0.25 mm. Most preferably, a thickness of a self-adhering layer can be about 0.1 mm to 0.2 mm.

Figure 8:
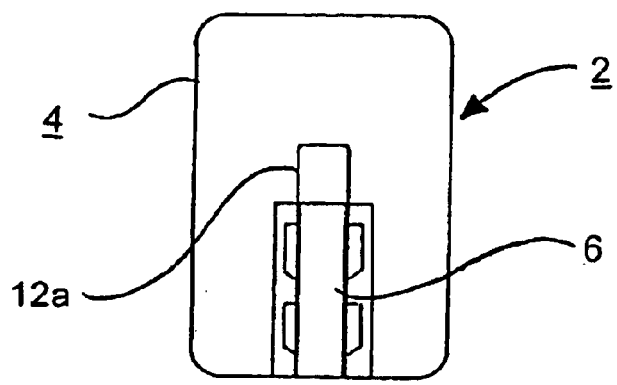
FIG. 8 is a top plan view of an application card of the present invention, illustrating details of the tear lines and tear reliefs incorporated into the self-adhering staple line reinforcement material.
Figure 9:
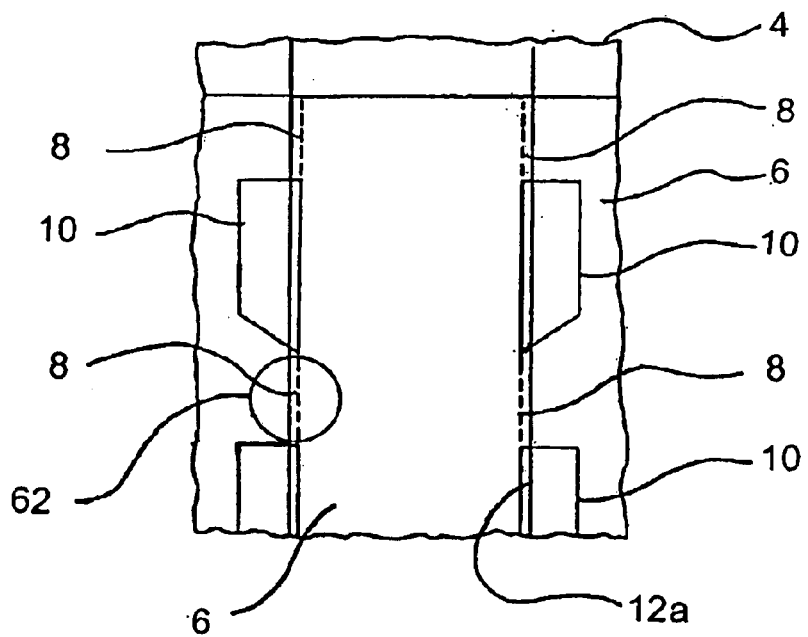
FIG. 9 is an enlarged partial top view of tear lines and tear reliefs shown in FIG. 8.

FIG. 8 is a top plan view of an apparatus 2 of the present invention. Shown are an application card 4 and a strip of reinforcement material 6, positioned within a first aperture 12a. FIG. 9 is an expanded view of FIG. 8, showing details of the aperture 12a and of the tear lines 8 and tear reliefs 10. The tear lines 8 and tear reliefs 10 are cut into the reinforcement material 6 by a laser, cutting dies, material etching, or any other suitable means. The tear lines and relief patterns provide a means for visually aligning a stapler to the reinforcement material.

Figure 10A:
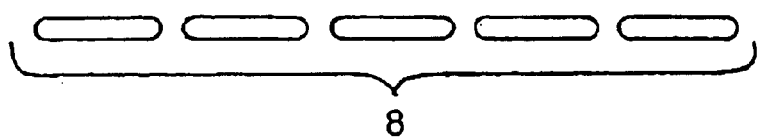
FIGS. 10A and 10B are further enlarged top views of the tear lines shown in FIG. 9.
Figure 10B:
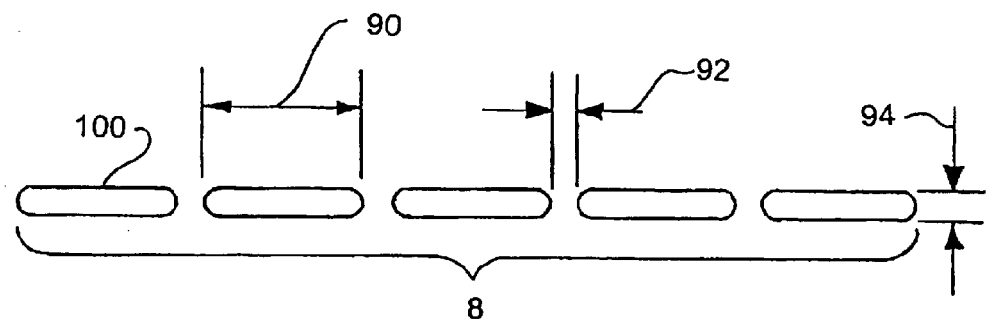
Figure 11:
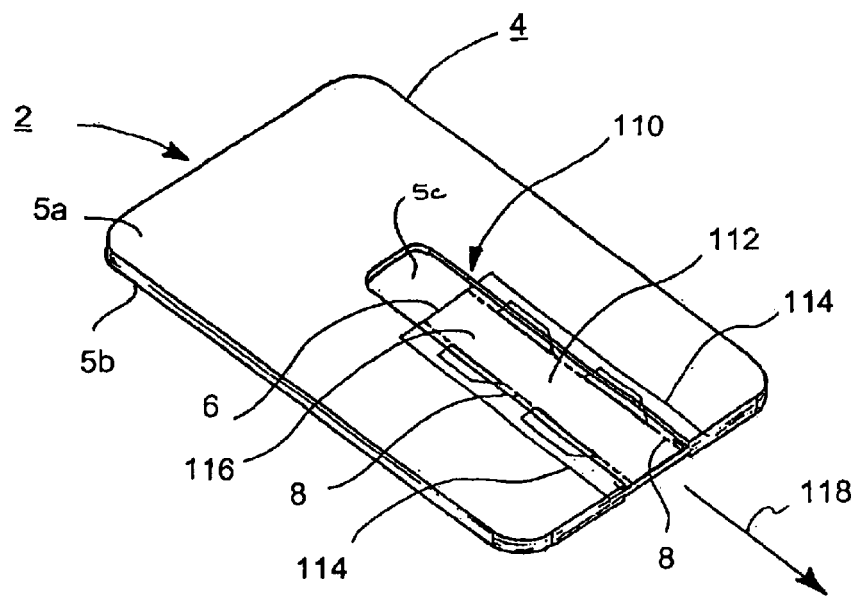
FIG. 11 is a three-quarter side isometric view of the apparatus of the present invention according to Example 1, comprising an application card and a strip of staple line reinforcement material having a first removable portion and a second retained portion.

FIG. 10A is an expanded view of the circled area 62 on FIG. 9. Shown in this detail is a typical cutting pattern used to generate a tear line 8. FIG. 10B is a detail of a typical tear line 8. Shown are cut-outs 100, cut-out lengths 90, spacing 92 between cut-outs 100 and a cut-out height 94. A typical cut-out length 90 can range from about 0.05 mm to about 10 mm or more, depending upon a specific stapler configuration and reinforcement material. For example cut-out length 90 can be about: 0.05 mm, 0.1 mm, 0.2 mm, 0.3 mm, 0.4 mm, 0.5 mm, 0.6 mm, 0.7 mm, 0.8 mm, 0.9 mm, 1 mm, up to about 10 mm. Preferably, cut-out length 90 can be about 1 mm to 7.5 mm. Most preferably, cut-out length 90 can be about 2 mm to 6 mm.

A typical spacing 92 between cut-outs 100 can range from about 0.05 mm to 0.4 mm or more, depending upon specific stapler configurations and reinforcement materials. For example, spacing 92 between cut-outs 100 can be about: 0.05 mm, 0.1 mm, 0.15 mm, 0.2 mm, 0.25 mm, 0.3 mm, 0.35 mm, or 0.4 mm. Preferably, spacing 92 between cut-outs 100 can be about 0.1 mm to 0.3 mm. Most preferably, spacing 92 between cut-outs 100 can be about 0.12 mm to 0.2 mm. Spacing 92, along with the number of cut-outs 100 relate to the force required to tear and separate the reinforcement material. This spacing is therefore tailored to give the desired tear force and is dependent upon the specific reinforcement material and material thickness.

A typical cut-out height 94 can range from about 0.05 mm to about 0.3 mm or more, depending upon specific method used for forming the cut-outs. For example, cut-out height 94 can be about: 0.05 mm, 0.1 mm, 0.15 mm, 0.2 mm, 0.25 mm, or 0.3 mm. Preferably, cut-out height 94 can be about 0.07 mm to 0.22 mm. Most preferably, cut-out height 94 can be about 0.08 mm to 0.12 mm.

Without intending to limit the present invention, the following examples specify how the present invention can be made and used.

EXAMPLE 1

A package for applying surgical staple reinforcement material to the arms of a commercially available stapler was constructed. The specific stapler, for which this package was configured for use, was a Model ETS 45 available from Ethicon, Somerville, N.J. The basic configuration of this example is shown in FIGS. 11 to 13A–13E. Shown is a package 2 for applying surgical staple reinforcement material to the arms of a surgical stapler. The package 2 comprised an application card 4, including a first portion 5a, a second portion 5b, and a landing 110 against support layer 5C. The package 2 further comprised a reinforcement material 6 having a first portion 112, adapted to be attached to the jaws of the aforementioned family of surgical staplers. The reinforcement material 6 had a second portion 114, attached to the application card 4. Tear lines 8 separated the first portion 112 and second portions 114 of the reinforcement material 6. An adhesive 116 was attached to the first portion 112 and second portion 114 of the reinforcement material 6. The attachment of the second portion 114 to the application card 6, resulted in the first portion 112 being positioned within the landing 110. The tear lines 8 allowed the first portion 112 to be separated laterally, in the direction depicted by element 118, from the second portion 114, after the adhesive 116 attached the first portion 112 to the arms of a Model ETS 45 surgical stapler available from Ethicon, Somerville, N.J.

Figure 12:
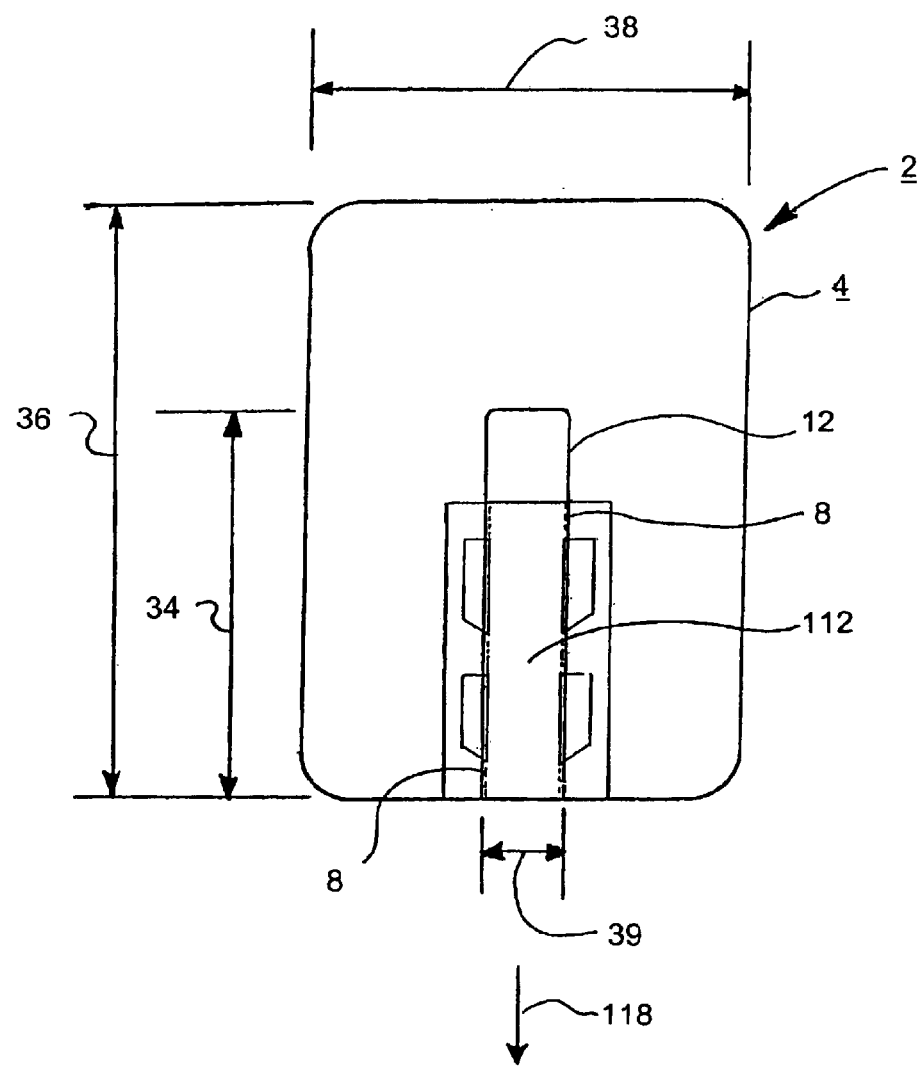
FIG. 12 is a top plan view of the apparatus of FIG. 11 having an aperture with a length and width.

As shown in FIG. 12, the application card 4 was constructed with an aperture 12. The aperture length 34 was about 67 mm and the aperture width 39 was about 13 mm. The application card 4 had a length 36 of about 103 mm and a width 38 of about 66 mm.

Figure 13A:
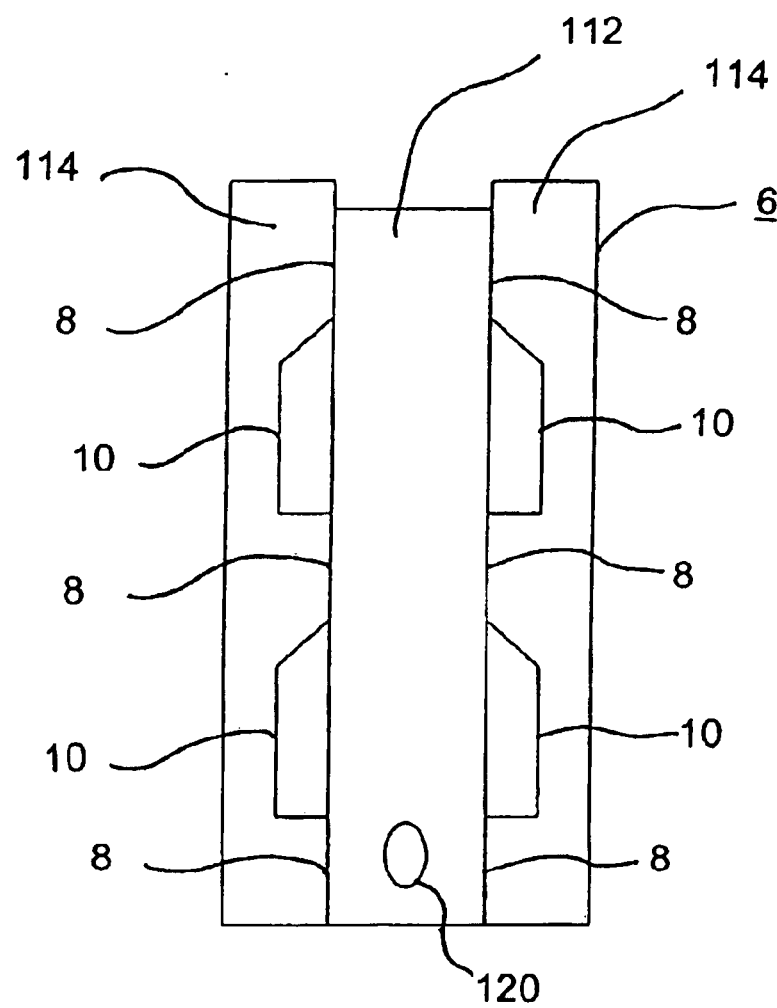
FIGS. 13A and 13B are top plan views of the reinforcement material of FIG. 11.
Figure 13B:
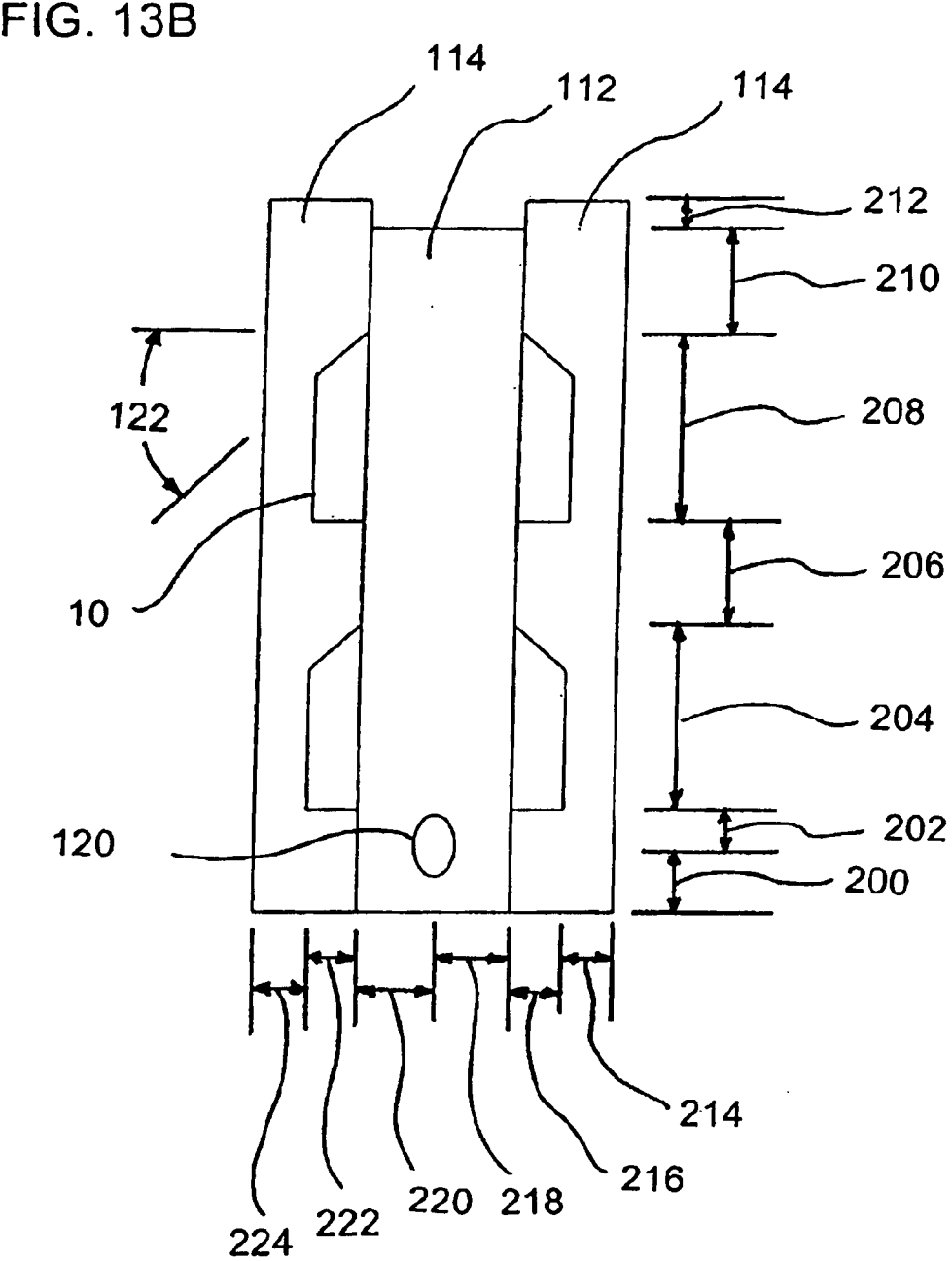
Figure 13C:
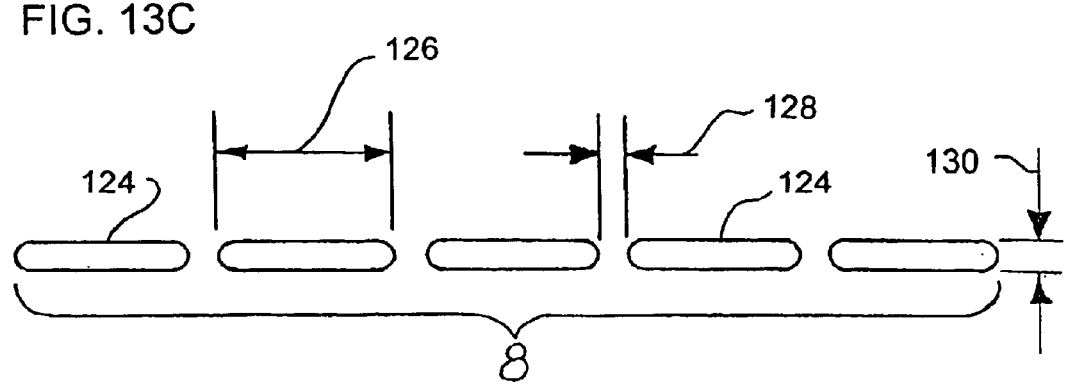
FIG. 13C is an enlarged partial top view of the tear lines shown in FIGS. 13A and 13B.

Details relating to the reinforcement material are shown in FIGS. 13A through C. Shown in FIG. 13A is a top view of the reinforcement material 6. Shown are tear lines 8 and tear reliefs 10 which define the first operative portion 112, adapted to be attached to the stapler arm. Within the first portion 112 was a optional clearance hole 120, designed to provide clearance for the raised scalpel blade stop located on the staple cartridge. Also shown are the second portions 114, which were attached the application card previously described. Detailed dimensions of the reinforcement material are shown in FIG. 13B. Element 200 was about 4.6 mm, element 202 was about 2.5 mm, element 204 was about 13.1 mm, element 206 was about 7 mm, element 208 was about 13.1 mm, element 210 was about 7 mm, element 212 was about 2 mm, element 214 was about 3.2 mm, element 216 was about 3.2 mm, element 218 was about 4.8 mm, element 220 was about 4.8 mm, element 222 was about 3.2 mm, and element 224 was about 3.2 mm. Elements 200 and 218 locate the approximate center of the oval shaped clearance hole 120, which had a long vertical axis of about 4.4 mm and a short horizontal axis of about 2.5 mm. The tear reliefs 10 were cut at an approximate 45 degree angle as depicted by element 122.

Shown in FIG. 13C are details of the tear lines 8, comprising a series of cut-outs 124. The cut out length 126 was about 1.3 mm, the cut out spacing 128 was about 0.13 mm, and the cut-out height 130 was about 0.13 mm. The reinforcement material 6 comprised expanded polytetrafluoroethylene (ePTFE) with a pressure sensitive adhesive applied to the surface contacted by the stapler jaws. The patterns shown in FIGS. 13 A, B and C were cut using a laser.

Figure 13D:
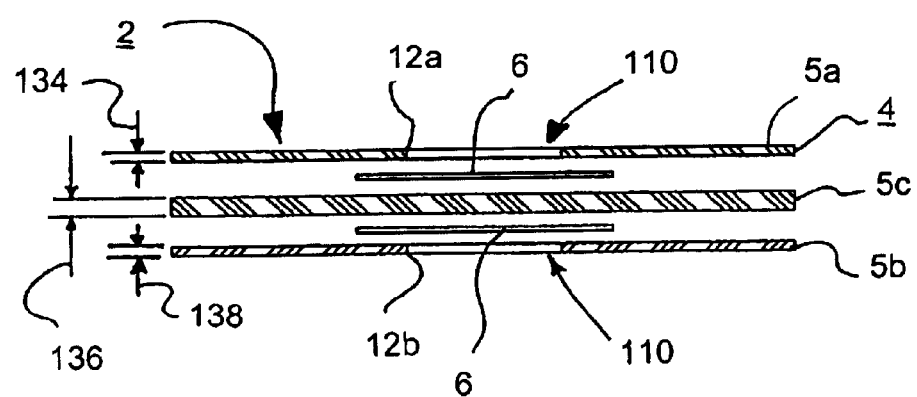
FIG. 13D is a front edge view showing the multi-layered construction of the application card of FIG. 11.

Shown in FIG. 13D is an edge front view of the package 2 of the present example. Shown are an application card 4, having a first portion 5a and a second portion 5b, each having an aperture 12a and 12b, respectively, and a support layer 5C. The support layer 5C supported two reinforcement materials 6, which resulted in two landings 110. The thicknesses 134, 136, 138 of the first portion, the support layer, and second portion were each about 0.75 mm. These three layers of the application card were laser cut from polycarbonate sheets available from McMaster-Carr Supply Company, Los Angeles Calif. The pre-cut reinforcement materials 6 were positioned onto the pre-cut support layer 132 and positioned within the pre-cut card apertures 12a and 12b. The layered assembly was then clamped together using six BC-20 or BC-50 binder clips, available from Officemate International Corporation, Edison, N.J. The six clips were positioned and spaced along the outer periphery of the stacked assembly. Pressure sensitive adhesive, which was pre-applied to the surfaces of the reinforcement materials adjacent to the apertures, attached the reinforcement material the cards.

Figure 13E:
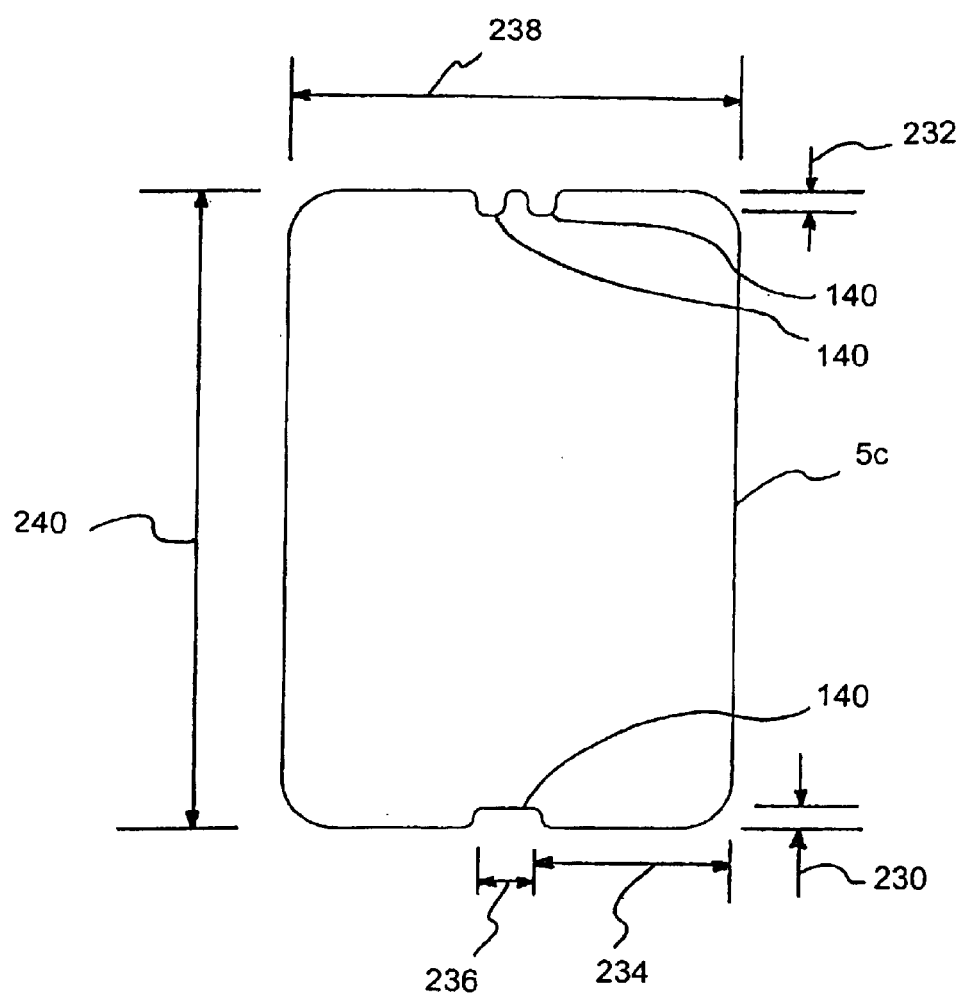
FIG. 13E is a top plan view of a support layer of the apparatus of FIG. 11.

Details of the support layer are shown in FIG. 13E. Shown is the support layer 5C with clearance reliefs 140. The reliefs 140 were configured to allow clearance between the stapler jaw pivot and the layered applicator package. Element 230 was about 3 mm, element 232 was about 3 mm, element 234 was about 29 mm, element 236 was about 9 mm, overall length 240 was about 103 mm, and the overall width 238 was about 66 mm.

EXAMPLE 2

A package was constructed to apply surgical staple reinforcement material to the arms of a Model ETS 45 surgical stapler available from Ethicon, Somerville, N.J. The basic configuration of this example is shown in FIG. 14. Shown is a package 2 for applying surgical staple reinforcement material to the arms of a surgical stapler. The package 2 comprised an application card 4, with a first portion 5a, a second portion 5b, and a landing 110 against support layer 5C. The package 2 further comprised a reinforcement material 6 having a first portion 112 adapted to be attached to the jaws of the aforementioned family of surgical staplers. The reinforcement material 6 had a second portion 114, attached to the application card 4. Tear lines 8 separated the first portion 112 and second portions 114 of the reinforcement material 6. An adhesive 116 was attached to the first portion 112 and second portion 114 of the reinforcement material 6. The attachment of the second portion 114 to the application card 6 resulted in the first portion 112 being positioned within the landing 110. The tear lines 8 allowed the first portion 112 to be separated laterally, in the direction depicted by element 118, from the second portion 114, after the adhesive 116 attached the first portion 112 to the arms of the surgical stapler.

The package 2 of the present invention incorporated four sets of alignment, press-fit posts 150. These elements 150 ensured the proper alignment of the first portion 5a, to the second portion 5b. Once aligned, the first and second portions 5a and 5b were press-fit together, sandwiching and securing a support layer 5C and two reinforcement materials 6, between the portions 5a and 5b. Two of the press-fit alignment posts incorporated reinforcement material alignment and securing features, shown as radii 152. As shown in subsequent Figures, these radii 152 engage similar radii cut into the retained 114 portions of the reinforcement material 6. This "inter-locking" feature aligns and enhances the securement of the retained portion 114 to portions 5a and 5b 4 when the lateral tearing force 118 is applied to the reinforcement material.

Figure 15:
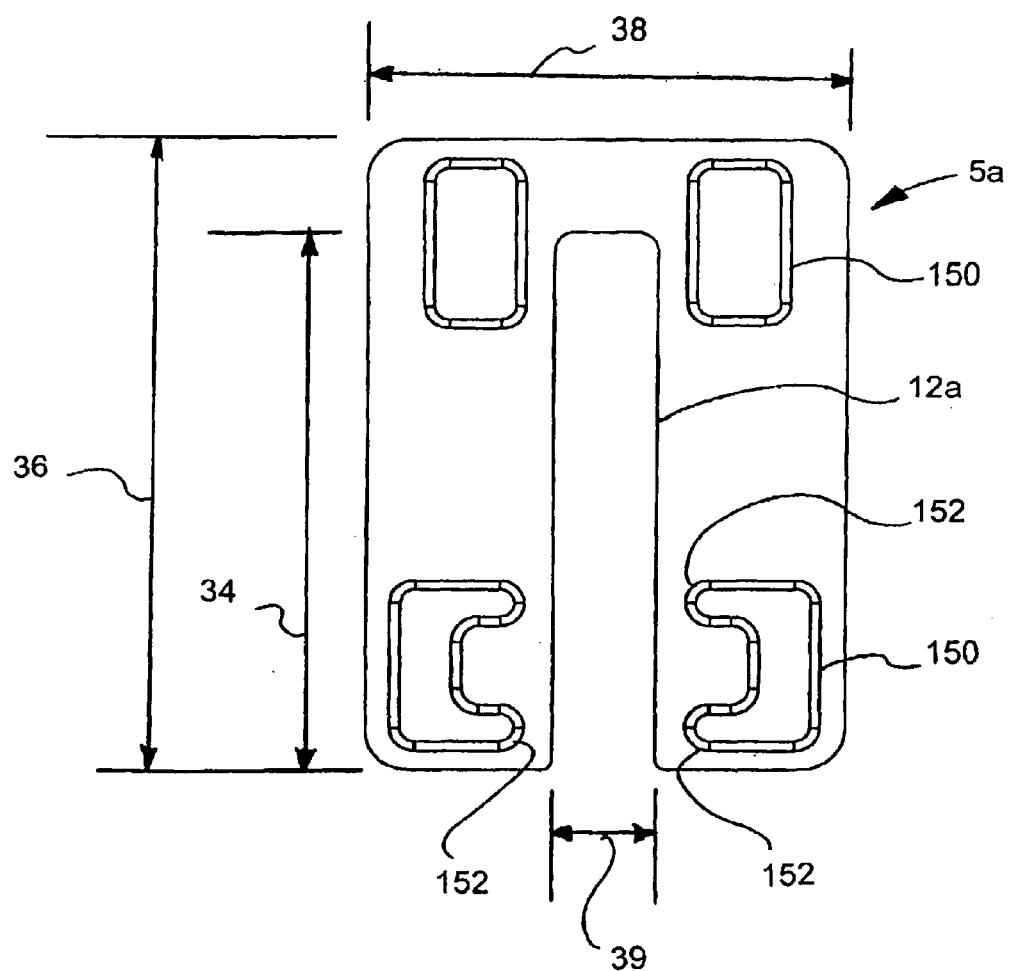
FIG. 15 is a top plan view of one portion of the application card of FIG. 14 having an aperture with a length and width.

FIG. 15 illustrates first portion 5a having a first aperture 12a. Each of the portions 5a and 5b of the application card 4 was constructed with an aperture 12. The aperture length 34 was about 67 mm and the aperture width 39 was about 13 mm. The application card 4 had a length 36 of about 104 mm and a width 38 of about 67 mm.

Figure 16A:
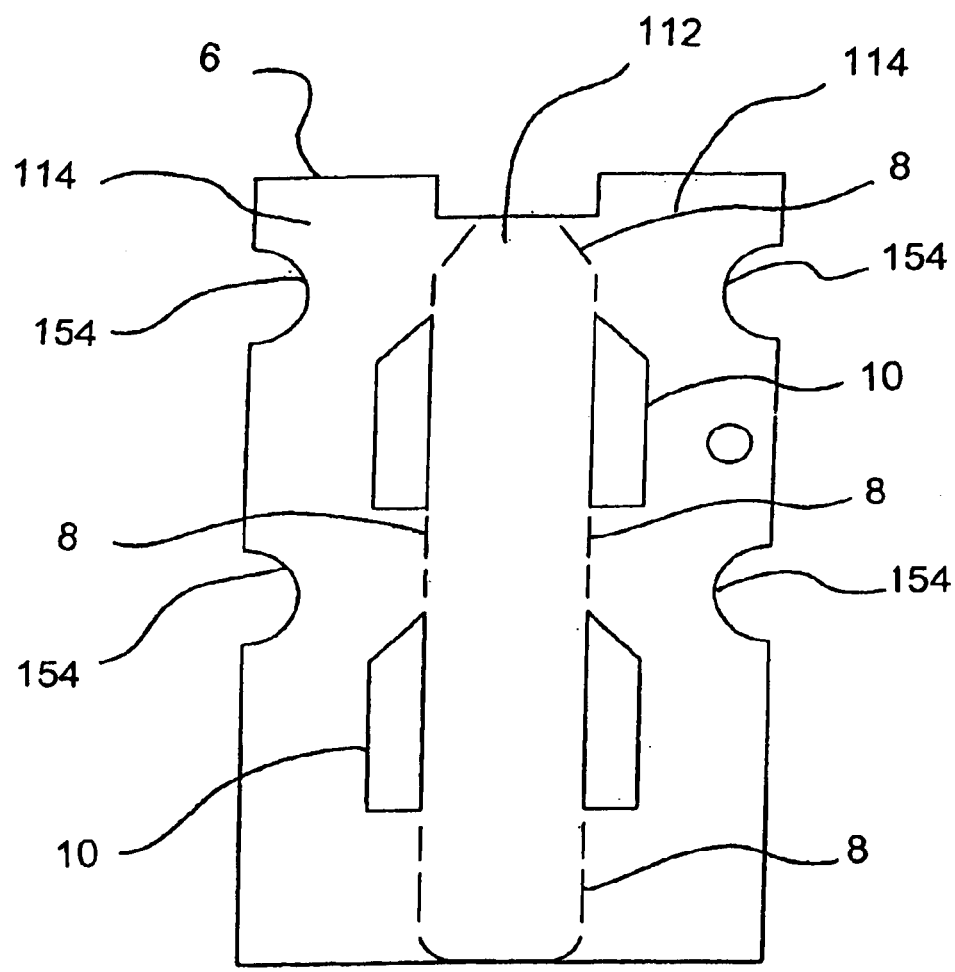
FIGS. 16A through D are top plan views of the reinforcement material of FIG. 14.

Details relating to the reinforcement material are shown in FIGS. 16A through E. Shown in FIG. 16A is a top view of the reinforcement material 6, dimensioned to be adapted to the cartridge portion of the stapler arm. Shown are tear lines 8 and tear reliefs 10 which define the first portion 112, adapted to be attached to the stapler arm. Also shown are the second portions 114, which were attached the application card previously described. The alignment and securing radii 154 were dimensioned to engage the similar radii formed into the card. The interference between the matching radii enhanced the retainment of the reinforcement material to the card during application of the lateral separation force. Typical radii 154 were about 3.2 mm.

Figure 16B:
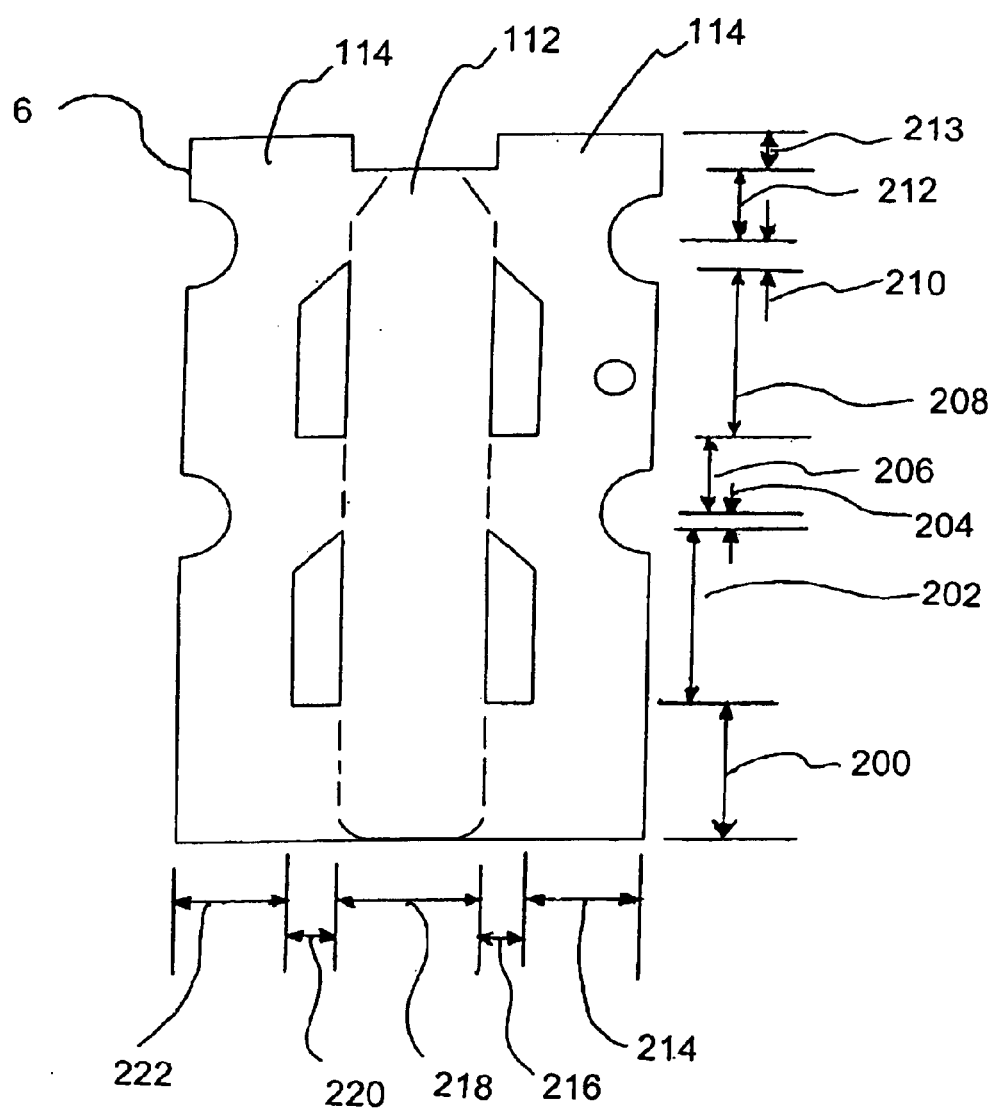

Detailed dimensions of the reinforcement material, dimensioned to be adapted to the cartridge, are shown in FIG. 16B. Element 200 was about 9.9 mm, element 202 was about 12.9 mm, element 204 was about 1.3 mm, element 206 was about 5.8 mm, element 208 was about 13.2 mm, element 210 was about 1.3 mm, element 212 was about 5.1 mm, element 213 was about 2.5 mm, element 214 was about 7.2 mm, element 216 was about 3.2 mm, element 218 was about 9.6 mm, element 220 was about 3.3 mm and element 222 was about 7.2. mm. The tear reliefs 10 were cut at an approximate 45 degree angle, as described in Example 1.

Figure 16C:
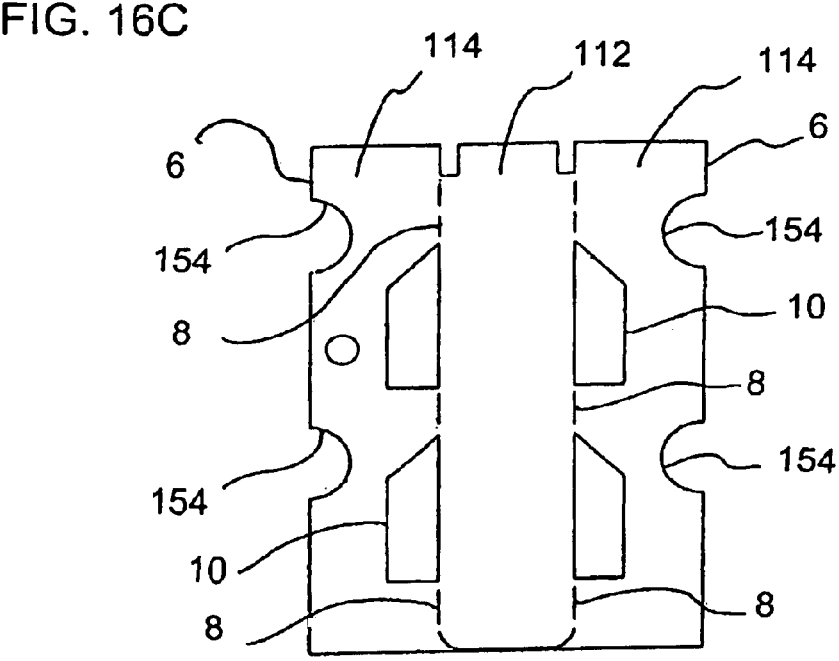

Shown in FIG. 16C is a top view of the reinforcement material 6, dimensioned to be adapted to the anvil portion of the stapler arm. Shown are tear lines 8 and tear reliefs 10 which define the first portion 112 adapted to be attached to the stapler arm. Also shown are the second portions 114, which were attached the application card previously described. The alignment and securing radii 154 were dimensioned to engage the similar radii formed into the card. The interference between the matching radii enhanced the retainment of the reinforcement material to the card during application of the lateral separation force. Typical radii 154 were about 3.2 mm.

Figure 16D:
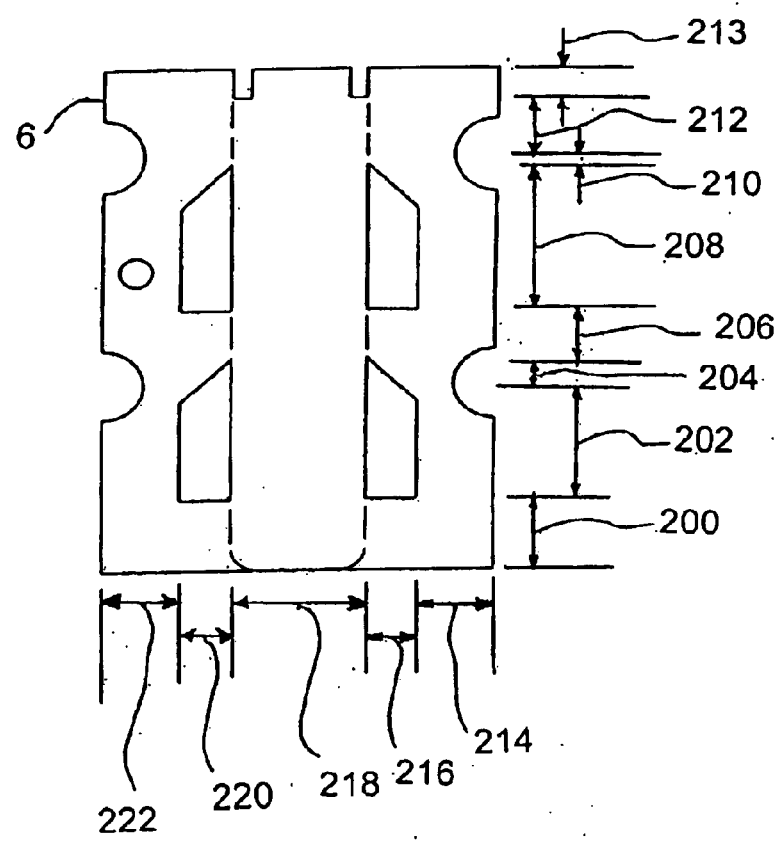

Detailed dimensions of the reinforcement material, dimensioned to be adapted to the anvil, are shown in FIG. 16D. Element 200 was about 6.1 mm, element 202 was about 10.4 mm, element 204 was about 2.5 mm, element 206 was about 4.3 mm, element 208 was about 12.7 mm, element 210 was about 0.8 mm, element 212 was about 5.1 mm, element 213 was about 2.7 mm, element 214 was about 6.1 mm, element 216 was about 3.9 mm, element 218 was about 10.4 mm, element 220 was about 4 mm, and element 222 was about 5.9 mm. The tear reliefs 10 were cut at an approximate 45 degree angle as described in Example 1.

Figure 16E:
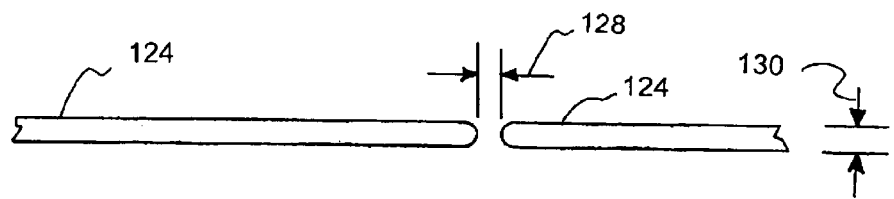
FIG. 16E is an enlarged partial top view of the tear lines shown in FIGS. 16A–16D.

Shown in FIG. 16E are details of the tear lines 8, comprising a series of cut-outs 124 separated by spaces 128. For the cartridge portion of the stapler arm (FIGS. 16 A and B), there were eighteen (18) spaces between cut-outs, twelve (12) having a length 92 of about 0.2 mm and the remaining six (6) having a length 92 of about 0.12 mm. For the anvil portion of the stapler arm (FIGS. 16C and D), there were fourteen (14) spaces between cut-outs, 12 having a length 92 of about 0.2 mm and the remaining two (2) having a length 92 of about 0.12 mm. The cut-out height 130 was about 0.1 mm. The reinforcement material 6 comprised expanded polytetrafluoroethylene (ePTFE) with a pressure sensitive adhesive applied to the surface contacted by the stapler jaws. The patterns shown in FIGS. 16A, B, C, D and E were cut using a laser.

Figure 16F:
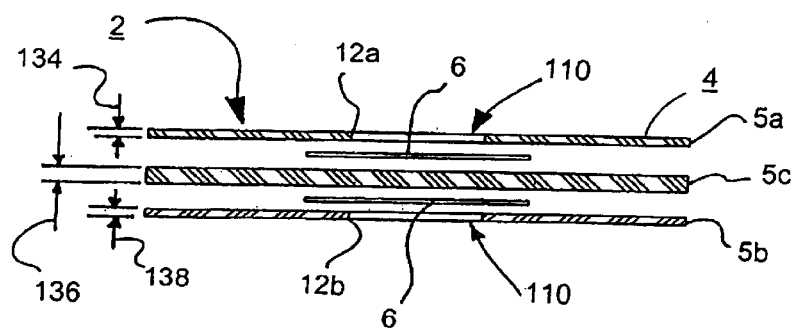
FIG. 16F is a partial front edge view showing the multi-layered construction of the application card of FIG. 14.

Shown in FIG. 16F is a simplified edge front view of the package 2 of the present example. Shown is an application card 4, having a first portion 5a, a second portion 5b, each having an aperture 12a and 12b, respectively, and support layer 5c. The support layer 5c supported two reinforcement materials 6, which resulted in two landings 110 positioned within apertures 12a and 12b. The thickness 134, 136, 138 of the first application card, support layer and second application card were each about 0.75 mm. The first application card, support layer and second application card were die cut and formed from polycarbonate, such as Makrofol R PCEE-112-8905 or GE Lexan R 8040. The pre-cut reinforcement materials 6 were positioned onto the pre-cut support layer 5c and positioned within the pre-cut card apertures 12. The layered assembly was then press-fit together. The pressure sensitive adhesive, which was pre-applied to the surfaces of the reinforcement materials adjacent to the apertures, attached the reinforcement material to the cards.

Figure 16G:
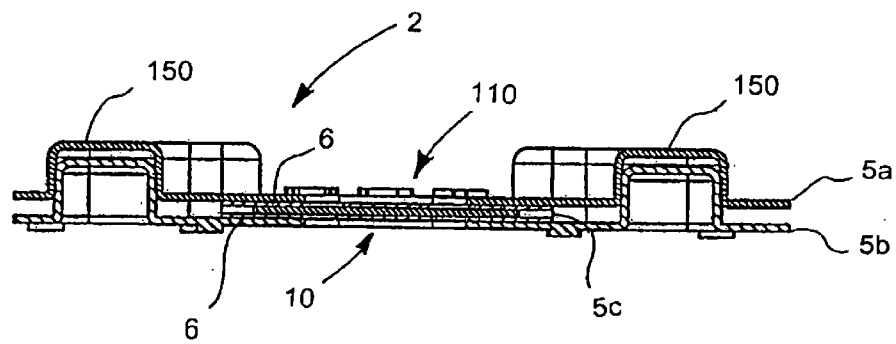
FIG. 16G is a front edge view of the entire application card of FIG. 14.

Shown in FIG. 16G is a detailed, cross-sectional edge front view of the package 2 of the present example. Shown is an application card 4 having a first portion 5a, a second portion 5b, two landings 110, a single support card 5c, and press-fit alignment posts 150. Two reinforcement materials 6 are mounted on the landings 110 of the card 4.

Figure 16H:
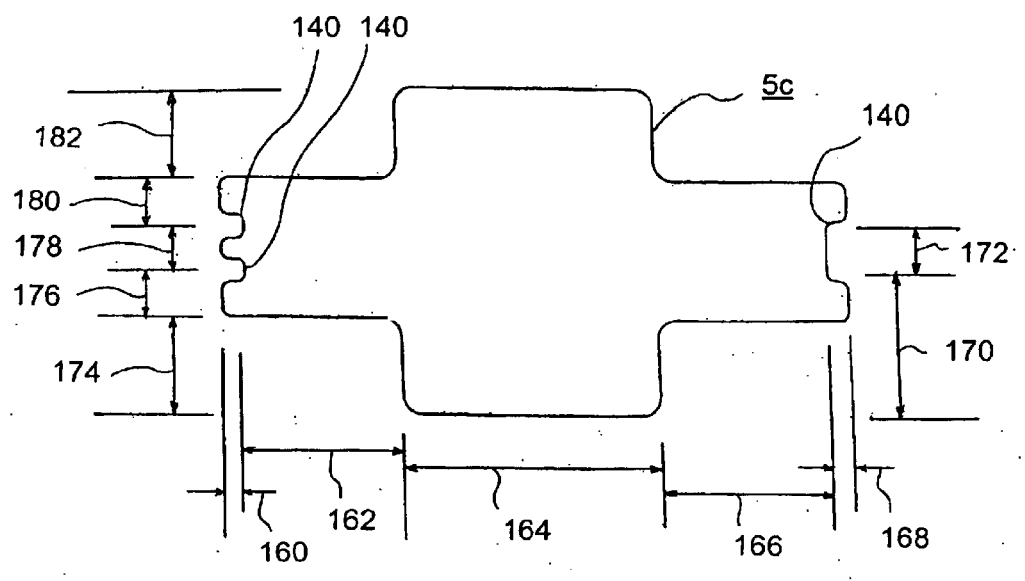
FIG. 16H is a top plan view of a support layer of the apparatus of FIG. 14.

Details of the support layer are shown in FIG. 16H. Shown is the support layer 5c with clearance reliefs 140. The reliefs 140 were configured to allow clearance between the stapler jaw pivot and the layered applicator package. Element 160 was about 4 mm, element 162 was about 30.5 mm, element 164 was about 43.6 mm, element 166 was about 26.9 mm, element 168 was about 3.2 mm, element 170 was about 23.6 mm, element 172 was about 10.4 mm, element 174 was about 16.5 mm, element 176 was about 8.4 mm, element 178 was about 7.9 mm, element 180 was about 8.3 mm and element 182 was about 16.1 mm.

The applicator card of the present invention was packaged into a sterile container forming a kit. Included in the kit was a separate, non-attached segment of foam, optionally used to reseat or improve attachment of the reinforcement material to the stapler jaw. The foam comprised a polyether—urethane, with approximate 1.6 # density, available from Pacfoam, Costa Mesa, Calif. The separate foam segment was approximately 104 mm wide by approximately 67 mm high and approximately 7 mm thick.

EXAMPLE 3

Figure 17:
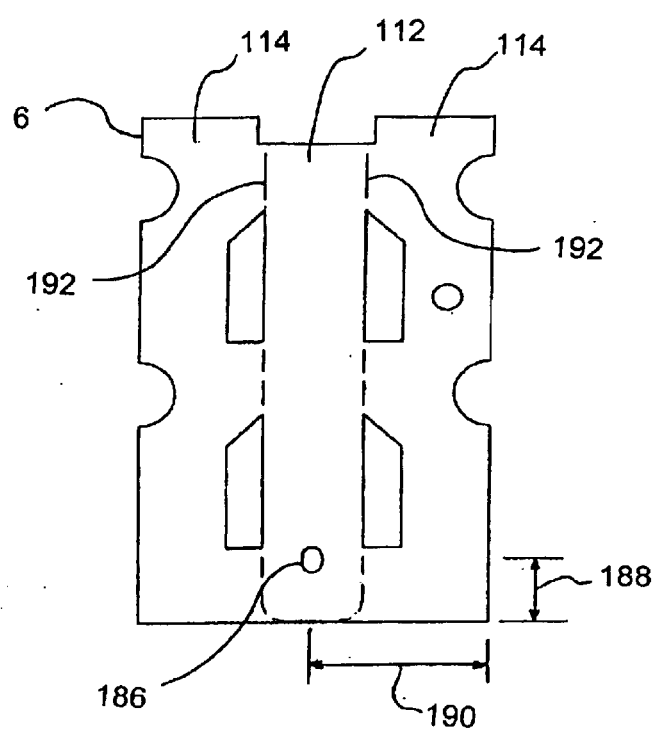
FIG. 17 is a top plan view of a reinforcement material for use with the present invention, according to Example 3.

A package was constructed to apply surgical staple reinforcement material to the arms of a Model EZ 45 surgical stapler available from Ethicon, Somerville, N.J. This package was similar to the package of Example 2 with the exception of details designed to accommodate the raised scalpel blade stop located on astapler cartridge. Shown on FIG. 17 is the cartridge portion of the reinforcement material 6 of the present example. Shown is the first removable portion 112 and the second retained portions 114 of the reinforcement material 6. Within the removable portion 112 was a clearance hole 186, designed to provide clearance for the raised scalpel blade stop located on the Model EZ 45 stapler cartridge. Elements 188 and 190 locate the approximate center of the oval shaped clearance hole 186, which had a long vertical axis of about 2.3 mm and a shorter horizontal axis of about 1.8 mm. Dimension 188 was about 5.8 mm and dimension 190 was about 15.3 mm. The tear lines on the cartridge reinforcement material, depicted as elements 192, were also altered as shown from the 45 degree configuration on FIGS. 16A and B.

Referring to FIG. 16E, the tear line pattern for the cartridge portion of the reinforcement material had 16 spaces between cut-outs, 10 having a length 92 of about 0.2 mm and the remaining 6 having a length 92 of about 0.12 mm. The tear line pattern for the anvil portion of the reinforcement material was as described in Example 2.

Figure 18:
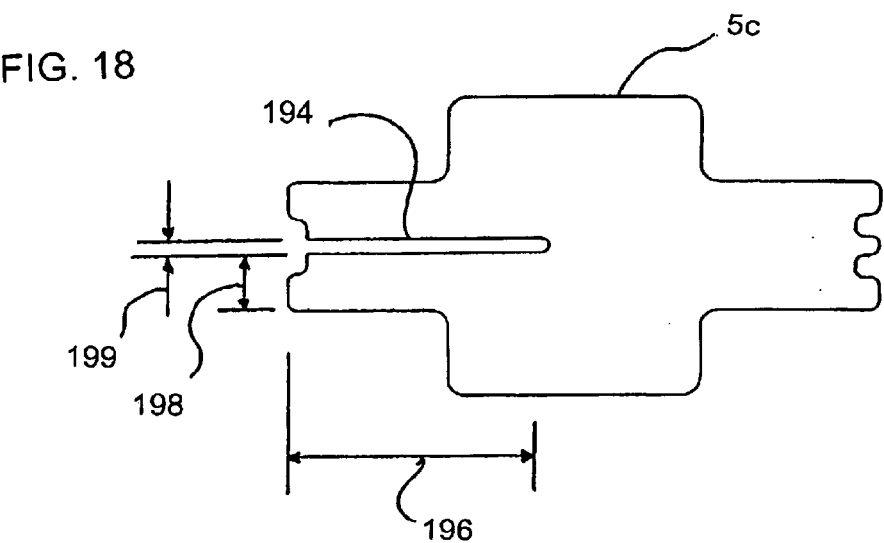
FIG. 18 is a top plan view of a support layer of the present invention, according to Example 3.

As shown in FIG. 18, the support layer 5c also incorporated a slot 194 to accommodate the raised scalpel blade stop located on the stapler cartridge. The slot 194 had a width 199 of about 3.5 mm, a length 196 of about 46 mm, and was located about the horizontal axis of the card, as shown by the dimension 198 of about 10.5 mm.

The package components of the present invention were designed to enhance assembly and alignment of the various layers. A pre-formed second portion, as described in Examples 1 and 2, was located onto an assembly fixture. A layer of reinforcement material was then placed onto the second portion with the self-adhesive layer down. The alignment radii on the card and reinforcement material insured proper alignment of the reinforcement material to the card aperture. The support layer was then placed onto the reinforcement material and was self-aligned by the press-fit posts, formed into the second portion. A second, pre-cut layer of reinforcement material was then placed onto the support layer with the self-adhesive layer facing up. The alignment radii on the bottom card insured proper positioning of the second layer of reinforcement material. The first portion was then aligned to the press-fit posts on the second portion. The layers were then simply pressed together. The compression was maintained by the interference fit between the posts formed into the first and second portions. The assembly was then packaged into a kit and sterilized.

EXAMPLE 4

As has been noted, it may be desirable to include a separate piece of foam or other resilient material with the package of the present invention to aid in reapplying staple reinforcement material that might separate from the stapler arms prior to application and/or to provide a surface against which to improve sealing of the reinforcement material prior to use.

Figure 19:
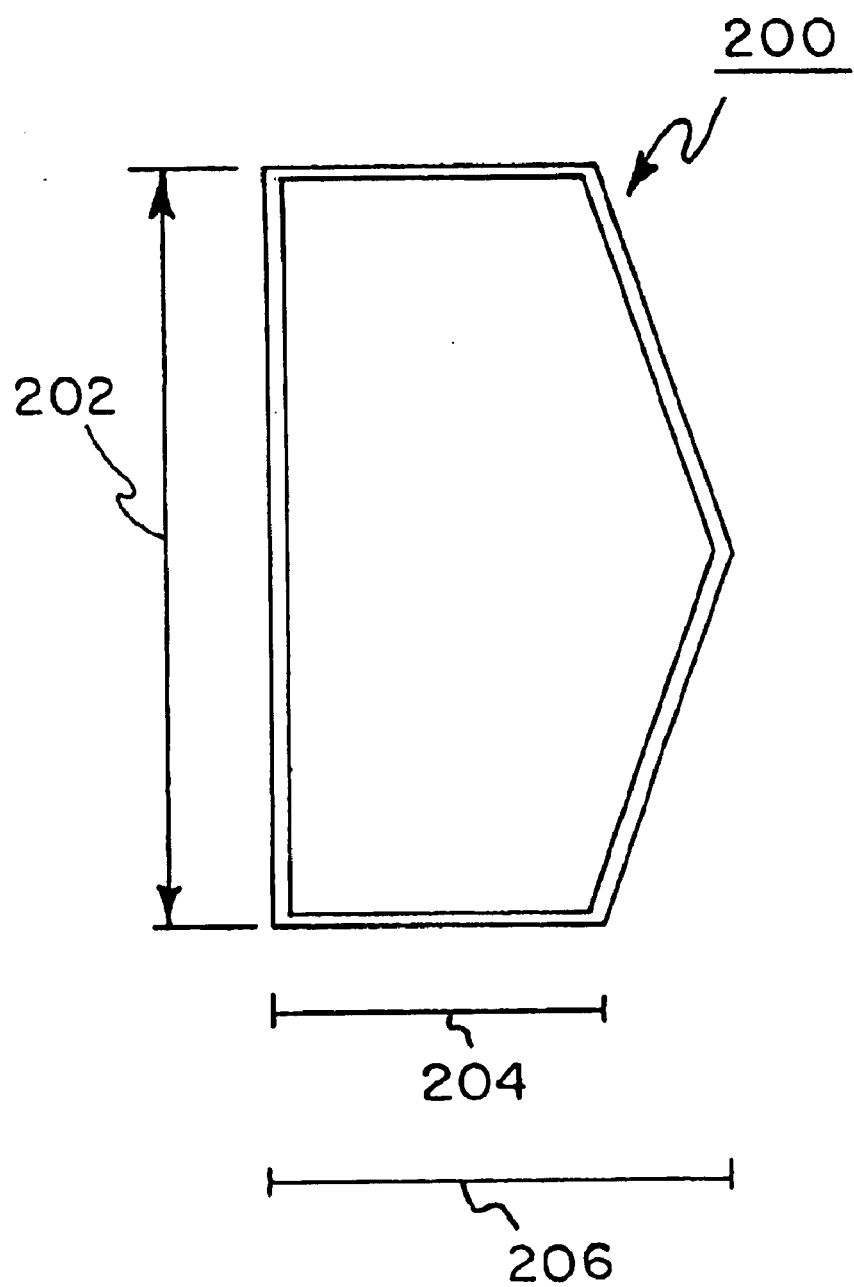
FIG. 19 is a top plan view of a resilient material that may be used with the present invention to supplement securement of the reinforcement material to stapler arms.

One example of such resilient material 200 is illustrated in FIG. 19. This material comprised a pentagonal shape of polyether-urethane foam, with about a 1.6 # density acquired from Pacfoam, Costa Mesa, Calif. This foam piece was about 10.5 cm along dimension 202, about 4.5 cm along dimension 204, and 6.5 cm along dimension 206. The foam was approximately 7 mm thick.

Figure 20A:
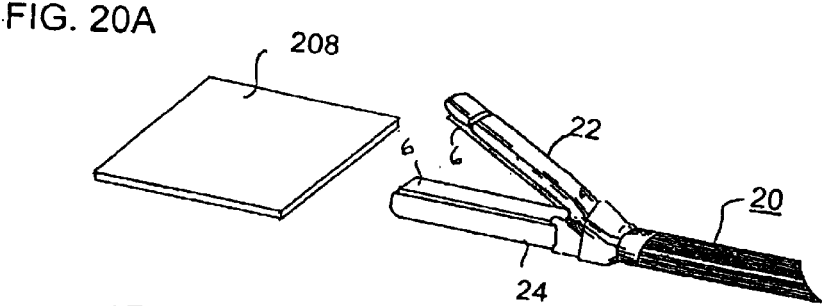
FIGS. 20A–20D are three-quarter side isometric views showing a process of supplementarily securing reinforcement material using another embodiment of the resilient material.
Figure 20B:
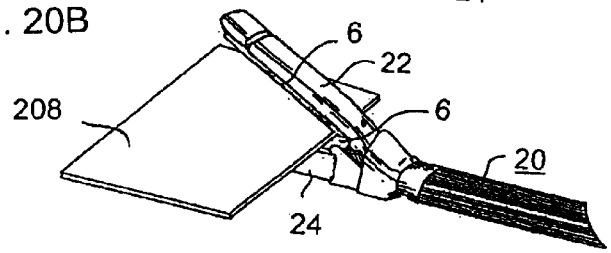
Figure 20C:
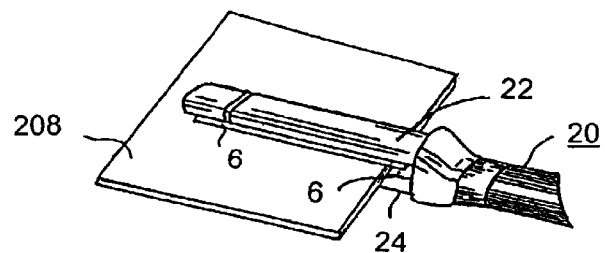
Figure 20D:
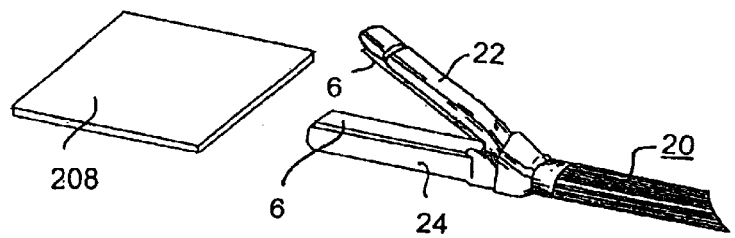

Use of similar resilient material 208 is illustrated in FIGS. 20A through 20D. A stapler assembly 20, having anvil 22 and cartridge 24, with staple reinforcement material 6 applied to each of the anvil 22 and cartridge 24, was positioned around the resilient material 208. As is shown in FIG. 20C, the jaws were then closed around the resilient material 208 and pressure was applied. The jaws were then opened and separated from the resilient material 208. This process provided more secure attachment of the reinforcement material 6 to the jaws.

Figure 21:
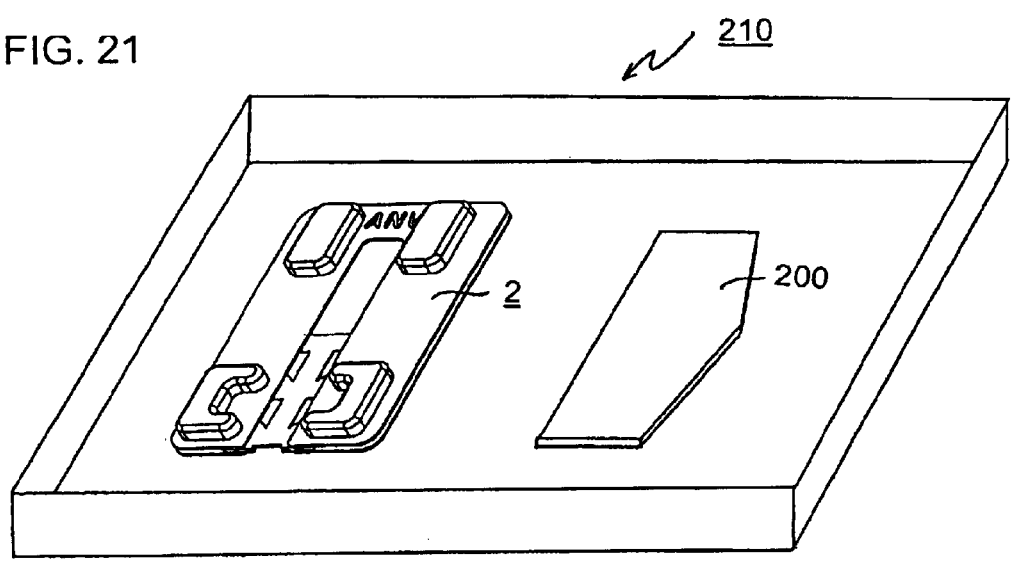
FIG. 21 is a three-quarter side isometric view showing a kit including the apparatus of the present invention and a separate resilient material.

FIG. 21 illustrates how a kit 210 can be packaged including both the apparatus of the present invention and resilient material 200.

While particular embodiments of the present invention have been illustrated and described herein, the present invention should not be limited to such illustrations and descriptions. It should be apparent that changes and modifications may be incorporated and embodied as part of the present invention within the scope of the following claims.

What is claimed is:

1. A package for applying surgical staple reinforcement material to arms of a surgical stapler comprising:

an application card;

staple reinforcement material having a first portion adapted to be attached to the arms of the surgical stapler, a second portion adapted to be attached to the application card, and tear lines separating the first portion and the second portion;

an adhesive to attach the first portion of staple reinforcement material to the stapler arms;

wherein the tear lines on the staple reinforcement material allow the first portion of staple reinforcement material to be separated laterally from the second portion once the adhesive attaches the first portion of the staple reinforcement material to the arms of the surgical stapler; and wherein the application card includes a notch therein to assist in aligning the stapler arms with the staple reinforcement material.

2. The package of claim 1 wherein the application card includes a landing; and wherein the second portion of the staple reinforcement material is attached to application card so as to position the first portion within the landing.

3. The package of claim 2 wherein the landing further comprises:

a first layer having an aperture;

the staple reinforcement material having a first surface and a second opposing surface;

the first surface of the staple reinforcement material exposed within the aperture; and the second opposing surface of the staple reinforcement material in contact with a support layer.

4. The package of claim 3 wherein the staple reinforcement material is attached to the first layer.

5. The package of claim 3 wherein the staple reinforcement material is attached to the support layer.

6. The package of claim 1 further comprising:

a support layer; and the staple reinforcement material attached to the support layer.

7. The package of claim 1 wherein the second portion of staple reinforcement material being adhered directly to the application card.

8. The package of claim 1 wherein the application card comprises at least two portions that are joined together.

9. The package of claim 8 wherein the two portions of the application card are attached together through interlocking posts.

10. The package of claim 9 wherein the staple reinforcement material is at least partially held in place on the application card through cut-outs aligned with the interlocking posts.

11. A kit comprising the package of claim 1; and a separate resilient material.

12. The kit of claim 11 wherein the resilient material comprises a foam.

13. A package for applying surgical staple reinforcement material to arms of a surgical stapler comprising:

an application card;

staple reinforcement material having a first portion adapted to be attached to the arms of the surgical stapler, a second portion adapted to be attached to the application card, and tear lines separating the first portion and the second portion;

an adhesive to attach the first portion of staple reinforcement material to the stapler arms;

wherein the tear lines on the staple reinforcement material allow the first portion of staple reinforcement material to be separated laterally from the second portion once the adhesive attaches the first portion of the staple reinforcement material to the arms of the surgical stapler;

wherein the application card comprises at least two portions that are joined together; and wherein the two portions of the application card are attached together through interlocking posts.

14. The package of claim 13 wherein the staple reinforcement material is at least partially held in place on the application card through cut-outs aligned with the interlocking posts.

15. A kit for applying surgical staple reinforcement material to arms of a surgical stapler comprising:

a package comprising an application card; staple reinforcement material having a first portion adapted to be attached to the arms of the surgical stapler, a second portion adapted to be attached to the application card, and tear lines separating the first portion and the second portion; an adhesive to attach the first portion of staple reinforcement material to the stapler arms; and wherein the tear lines on the staple reinforcement material allow the first portion of staple reinforcement material to be separated laterally from the second portion once the adhesive attaches the first portion of the staple reinforcement material to the arms of the surgical stapler; and a separate resilient material comprising a foam.

16. A package for applying surgical staple reinforcement material to arms of a surgical stapler comprising:

an application card;

staple reinforcement material having a first portion adapted to be attached to the arms of the surgical stapler, a second portion adapted to be attached to the application card, and tear lines separating the first portion and the second portion;

an adhesive to attach the first portion of staple reinforcement material to the stapler arms;

wherein the tear lines on the staple reinforcement material allow the first portion of staple reinforcement material to be separated laterally from the second portion once the adhesive attaches the first portion of the staple reinforcement material to the arms of the surgical stapler;

wherein the application card includes a landing;

wherein the second portion of the staple reinforcement material is attached to application card so as to position the first portion within the landing; and wherein the landing further comprises a first layer having an aperture;

the staple reinforcement material having a first surface and a second opposing surface;

the first surface of staple reinforcement material exposed within the aperture; and the second opposing surface of the staple reinforcement material in contact with a support layer.

17. The package of claim 16 wherein the staple reinforcement material is attached to the first layer.

18. The package of claim 17 wherein the staple reinforcement material is attached to the support layer.

* * * * *